(12) United States Patent
Axelson, Jr. et al.

(10) Patent No.: US 8,617,173 B2
(45) Date of Patent: Dec. 31, 2013

(54) SYSTEM FOR ASSESSING A FIT OF A FEMORAL IMPLANT

(71) Applicant: Stryker Leibinger GmbH & Co. KG, Freiburg (DE)

(72) Inventors: Stuart L. Axelson, Jr., Succasunna, NJ (US); Jens Rueber, Freiburg (DE); Jose Luis Moctezuma de la Barrera, Freiburg (DE); Peter Zimmermann, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 0 days.

(21) Appl. No.: 13/753,157

(22) Filed: Jan. 29, 2013

(65) Prior Publication Data

US 2013/0144352 A1    Jun. 6, 2013

Related U.S. Application Data

(62) Division of application No. 12/221,858, filed on Aug. 6, 2008, now Pat. No. 8,382,765.

(60) Provisional application No. 60/963,738, filed on Aug. 7, 2007, provisional application No. 60/963,916, filed on Aug. 8, 2007.

(51) Int. Cl.
- *A61B 17/58* (2006.01)
- *A61B 17/60* (2006.01)
- *A61F 2/00* (2006.01)

(52) U.S. Cl.
USPC .............................. 606/88; 606/86 R; 606/87

(58) Field of Classification Search
USPC .......................................... 606/86 R, 87, 88
See application file for complete search history.

(56) References Cited

U.S. PATENT DOCUMENTS

| | | | |
|---|---|---|---|
| 4,323,459 | A | 4/1982 | Quinlan |
| 4,396,945 | A | 8/1983 | DiMatteo et al. |

(Continued)

FOREIGN PATENT DOCUMENTS

| | | |
|---|---|---|
| DE | 39 04 595 | 4/1990 |
| EP | 0 705 074 | 5/2000 |

(Continued)

OTHER PUBLICATIONS

"Kinematik Approach to Hip Navigation," Jose Moctezuma Jul. 24, 2002 (10 pages).

(Continued)

*Primary Examiner* — Andrew Yang
(74) *Attorney, Agent, or Firm* — Howard & Howard Attorneys PLLC

(57) ABSTRACT

A system for virtually planning a size and position of a prosthetic implant for a bone on a patient includes a database containing pre-defined form factor information for a plurality of different implants and a circuit for obtaining surface shape information of the bone. The system further includes a circuit for defining baseline location parameters for an implant location in relation to a virtual representation of the bone based on the surface shape information and a circuit for assessing a fit calculation of each implant in relation to the virtual representation of the bone based on the form factor in formation and a plurality of fit factors at each of a plurality of incremental positions in relation to the bone. Still further, the system includes a circuit for selecting a best fit implant size and position from all of the fit calculations.

12 Claims, 19 Drawing Sheets

(56) References Cited

U.S. PATENT DOCUMENTS

| | | |
|---|---|---|
| 4,722,056 A | 1/1988 | Roberts et al. |
| 4,869,247 A | 9/1989 | Howard, III et al. |
| 4,923,459 A | 5/1990 | Nambu |
| 4,945,914 A | 8/1990 | Allen |
| 4,951,653 A | 8/1990 | Fry et al. |
| 4,991,579 A | 2/1991 | Allen |
| 5,016,639 A | 5/1991 | Allen |
| 5,094,241 A | 3/1992 | Allen |
| 5,097,839 A | 3/1992 | Allen |
| 5,119,817 A | 6/1992 | Allen |
| 5,142,930 A | 9/1992 | Allen et al. |
| 5,178,164 A | 1/1993 | Allen |
| 5,186,174 A | 2/1993 | Schlondorff et al. |
| 5,197,488 A | 3/1993 | Kovacevic |
| 5,198,877 A | 3/1993 | Schulz |
| 5,211,164 A | 5/1993 | Allen |
| 5,222,499 A | 6/1993 | Allen et al. |
| 5,230,338 A | 7/1993 | Allen et al. |
| 5,305,203 A | 4/1994 | Raab |
| 5,309,101 A | 5/1994 | Kim et al. |
| 5,321,257 A | 6/1994 | Danisch |
| 5,383,454 A | 1/1995 | Bucholz |
| 5,394,875 A | 3/1995 | Lewis et al. |
| 5,397,329 A | 3/1995 | Allen |
| 5,494,034 A | 2/1996 | Schlondorff et al. |
| 5,515,160 A | 5/1996 | Schulz et al. |
| 5,520,694 A | 5/1996 | Dance et al. |
| 5,551,429 A | 9/1996 | Fitzpatrick et al. |
| 5,575,794 A | 11/1996 | Walus et al. |
| 5,590,215 A | 12/1996 | Allen |
| 5,595,193 A | 1/1997 | Walus et al. |
| 5,617,857 A | 4/1997 | Chader et al. |
| 5,622,170 A | 4/1997 | Schulz |
| 5,633,494 A | 5/1997 | Danisch |
| 5,638,819 A | 6/1997 | Manwaring et al. |
| 5,665,090 A | 9/1997 | Rockwood et al. |
| 5,665,092 A | 9/1997 | Mangiardi et al. |
| 5,695,501 A | 12/1997 | Carol et al. |
| 5,704,897 A | 1/1998 | Truppe |
| 5,711,299 A | 1/1998 | Manwaring et al. |
| 5,730,130 A | 3/1998 | Fitzpatrick et al. |
| 5,752,513 A | 5/1998 | Acker et al. |
| RE35,816 E | 6/1998 | Schulz |
| 5,769,789 A | 6/1998 | Wang et al. |
| 5,797,924 A | 8/1998 | Schulte et al. |
| 5,799,099 A | 8/1998 | Wang et al. |
| 5,851,183 A | 12/1998 | Bucholz |
| 5,871,445 A | 2/1999 | Bucholz |
| 5,880,976 A | 3/1999 | DiGioia, III et al. |
| 5,891,034 A | 4/1999 | Bucholz |
| 5,891,157 A | 4/1999 | Day et al. |
| 5,907,395 A | 5/1999 | Schulz et al. |
| 5,916,164 A | 6/1999 | Fitzpatrick et al. |
| 5,917,180 A | 6/1999 | Reimer et al. |
| 5,921,992 A | 7/1999 | Costales et al. |
| 5,954,648 A | 9/1999 | Van Der Brug |
| 5,970,499 A | 10/1999 | Smith et al. |
| 5,987,349 A | 11/1999 | Schulz |
| 5,995,738 A | 11/1999 | DiGioia, III et al. |
| 6,073,043 A | 6/2000 | Schneider |
| 6,073,044 A | 6/2000 | Fitzpatrick et al. |
| 6,081,336 A | 6/2000 | Messner et al. |
| 6,112,113 A | 8/2000 | Van Der Brug et al. |
| 6,127,672 A | 10/2000 | Danisch |
| 6,205,411 B1 | 3/2001 | DiGioia, III et al. |
| 6,338,716 B1 | 1/2002 | Hossack et al. |
| 6,385,475 B1 | 5/2002 | Cinquin et al. |
| 6,390,982 B1 | 5/2002 | Bova et al. |
| 6,430,434 B1 | 8/2002 | Mittelstadt |
| 6,453,190 B1 | 9/2002 | Acker et al. |
| 6,563,107 B2 | 5/2003 | Danisch et al. |
| 6,569,169 B2 | 5/2003 | De LaBarrera et al. |
| 6,595,997 B2 | 7/2003 | Axelson, Jr. et al. |
| 6,676,706 B1 | 1/2004 | Mears et al. |
| 6,695,850 B2 | 2/2004 | Diaz |
| 6,711,431 B2 | 3/2004 | Sarin et al. |
| 6,859,661 B2 | 2/2005 | Tuke |
| 6,877,239 B2 | 4/2005 | Leitner et al. |
| 6,923,817 B2 | 8/2005 | Carson et al. |
| 7,209,776 B2 | 4/2007 | Leitner |
| 7,319,897 B2 | 1/2008 | Leitner et al. |
| 7,331,932 B2 | 2/2008 | Leitner |
| 2001/0034530 A1 | 10/2001 | Malackowski et al. |
| 2002/0133160 A1 | 9/2002 | Axelson, Jr. et al. |
| 2003/0105470 A1 | 6/2003 | White |
| 2003/0153978 A1 | 8/2003 | Whiteside |
| 2004/0102792 A1 | 5/2004 | Sarin et al. |
| 2004/0106869 A1 | 6/2004 | Tepper |
| 2004/0117026 A1 | 6/2004 | Tuma et al. |
| 2004/0171924 A1 | 9/2004 | Mire et al. |
| 2004/0171929 A1 | 9/2004 | Leitner et al. |
| 2004/0193211 A1 | 9/2004 | Voegelle et al. |
| 2004/0199204 A1 | 10/2004 | Voegelle et al. |
| 2004/0230199 A1 | 11/2004 | Jansen et al. |
| 2005/0065617 A1 | 3/2005 | de la Barrera |
| 2005/0119661 A1 | 6/2005 | Hodgson et al. |
| 2005/0203383 A1 | 9/2005 | de la Barrera |
| 2005/0251065 A1 | 11/2005 | Henning et al. |
| 2006/0100504 A1 | 5/2006 | Jansen et al. |
| 2007/0038223 A1 | 2/2007 | Marquart et al. |

FOREIGN PATENT DOCUMENTS

| | | |
|---|---|---|
| EP | 1 417 941 | 5/2004 |
| JP | 3-267054 | 11/1991 |
| JP | 06-282889 | 10/1994 |
| JP | 06-282890 | 10/1994 |
| WO | WO 90/05494 | 5/1990 |
| WO | WO 00/39576 | 7/2000 |
| WO | WO 03/079940 | 10/2003 |
| WO | WO 2005/072629 | 8/2005 |

OTHER PUBLICATIONS

"Surgical Steps for Computer Assisted Total Hip Arthroplasty," HipTrac V1.0 Jose Luis Moctezuma de la Barrera Jun. 4, 2000 (6 pages).

"Software Requirements Specification (SRS) Image Enhanced Knee Navigation, #1728," Richard Aschenbrenner Jun. 23, 2003 (46 pages).

"Rx90® Total Hip System Acetabular Series," Biomet Orthopedics, Inc. 2001 (11 pages).

"Radiographic and Non-Invasive Determination of the Hip Joint Center Location: Effect on Hip Joint Angles," R.N. Kirkwood et al. Oct. 16, 2003 (3 pages).

"Hip Joint Anatomy,"http://vv.totaljoints.info/HIPJOINT_anatomydetails.htm Oct. 7, 2003 (3 pages).

"Virtual Planning of Hip Operations and Individual Adaption of Endoprostheses in Orthopaedic Surgery," H. Handels et al. (12 pages), Aug. 1999.

"Inclination," http://www.gentili.net/thr/inclinat.htm Oct. 16, 2003 (1 page).

"Hip: Functional Method," http://kwon3d.com/manuals/kwon3d30/modeling/hip_func.html Oct. 16, 2003 (4 pages).

Web page from http://www.totaljoints.info/NORMALHIPJOINTIMAGE.jpg Oct. 7, 2003 (1 page).

Web page from http://www.totaljoints.info/REPLACEDHIPJOINTIMAGE.jpg Oct. 7, 2003 (1 Page).

Web page from http://www.totaljoints.info/ANT_approach2.jpg Oct. 7, 2003 (I page).

Web page from http://www.totaljoints.info/POST_approach2.jpg Oct. 7, 2003 (1 page).

Birkfellner et al., "Evaluation and Detection of Systematic Distortions in DC-pulsed Electromagnetic Position Sensing Devices," Elsevier Science B. V., 1998, p. 927-928 (2 pages).

Kirsch et al., "Miniaturized Five Degree-of-Freedom Magnetic Tracker", Elsevier Science B.V., 1998, p. 928.

Birkfellner et al., "Systematic Distortions in Magnetic Position Digitizers," Med. Phys. 25 (11), pp. 2242-2248 (Nov. 1998).

(56) References Cited

OTHER PUBLICATIONS

Livingston et al., "Magnetic Tracker Calibration for Improved Augmented Reality Registration," Presence, vol. 6, No. 5, pp. 532-546 (Oct. 1997).
State et al., "Superior Augmented Reality Registration by Integrating Landmark Tracking and Magnetic Tracking," Proceedings of SIGGRAPH 96 (New Orleans, LA, Aug. 4-9, 1996). In Computer Graphics Proceedings, Annual Conference Series, pp. 429-438.
Birkfellner et al., "Calibration of Tracking Systems in a Surgical Environment," IEEE Tansactions on Medical Imaging, Nov. 17, 1998, pp. 1-6.
Birkfellner et al., "Evaluation of Magnetic Position Digitizers for Computer Assisted Surgery," Comput. Aided Surg. 2(3/4), 225 (1997).
Applied Neurophysiology, Journal of Stereotactic and Functional Neurosurgery, Proceedings of the Meeting of the American Society for Stereotactic and Functional Neurosurgery, Montreal, Quebec, (Jun. 3-6, 1987) Jan. 1998.
Journal of Ultrasound in Medicine vol. 9, No. 9, (Sep. 1990), pp. 525-532.
IEEE Computer Graphics & Applications vol. 10, No. 3, (May 1990), pp. 43-51.
Journal of Neurosurgery vol. 72, No. 2, (Feb. 1990), pp. 355a.
Journal of Neurosurgery vol. 65, No. 4, (Oct. 1986), pp. 550-554, 557-559.
Journal of Neurosurgery vol. 57, No. 2, (Aug. 1982), pp. 157-163.
Neurosurgery vol. 10, No. 5, (May 1982), pp. 580-586.
Neurosurgery vol. 10, (Mar. 1982), pp. 375-379.
Guided Brain Operations E.A. Spiegel ISBN: 3805534515, (1982), pp. 23, 25, 28.
American Journal of Neuroradiology vol. 2, No. 2 (Mar./Apr. 1981), pp. 181-184.
Neurosurgery vol. 8, No. 1 (Jan. 1981), pp. 72-82.
Surgical Neurology vol. 14, No. 6, (Dec. 1980), pp. 451-464.
Investigative Radiology vol. 15, No. 4, (Jul./Aug. 1980), pp. 308-312.
Applied Neurophysiology vol. 43, No. 3-5, (1980), pp. 170-171, 172-173, 174-175.
Neurosurgery vol. 3, No. 2, (Sep./Oct. 1978), pp. 157-161.
Amin et al."Ultrasound Registration of the Bone Surface for Surgical Navigation," (Biomedical Paper, Computer Aided Surgery) 8:1-16 (2003), (16 pages).
Amstutz et al. "A-Mode Ultrasound-Based Registration in Computer-Aided Surgery of the Skull," Arch Otolaryngol Head Neck Surg, vol. 129, Dec. 2003, (pp. 1310-1316).
International Search Report and Written Opinion in PCT/US01/02166 dated Aug. 15, 2001.
International Search Report and Written Opinion in PCT/IB2005/004073 Dated Jun. 2, 2006.
English language abstract and machine-assisted translation for DE3904595 (C1), extracted from the espacenet.com database on May 20, 2013.
English language abstract and machine-assisted translation for EP1417941 (A1), extracted from the espacenet.com database on May 20, 2013.
English language abstract and machine-assisted translation for JP6282889 (A), extracted from the PAJ database on May 21, 2013.
Stereotactic & Functional Neurosurgery vol. 53, No. 3, (1989) pp. 197-201.
Journal of Ultrasound in Medicine vol. 9, No. 9, (Sep 90), pp. 525-532.
Ultrasound in Neurosurgery J.M. Rubin et al. ISBN: 0881675490, pp. 47-58, 1990.
Stereotactic & Functional Neurosurgery vol. 54-55, (1990), pp. 418-426, 471-476, 482-487, 488-492, 493-496, 497-500.
British Journal of Neurosurgery vol. 4, No. 3, (1990), pp. 193-197.
IEEE Computer Graphics & Applications vol. 10, No. 3, (May 90), pp. 43-51.
Journal of Neurosurgery vol. 72, No. 2, (Feb 90), pp. 355a.
IEEE Engineering in Medicine & Biology Society—Proceedings of 11th Annual International Conference, (1989), pp. 925, 926-927.
British Journal of Neurosurgery vol. 3, No. 5, (1989), pp. 561-568, 569-574.
British Journal of Neurosurgery vol. 3, No. 3, (1989), pp. 327-331.
Acta Neurochirurgica Supplementum 46, (1989), pp. 112-114.

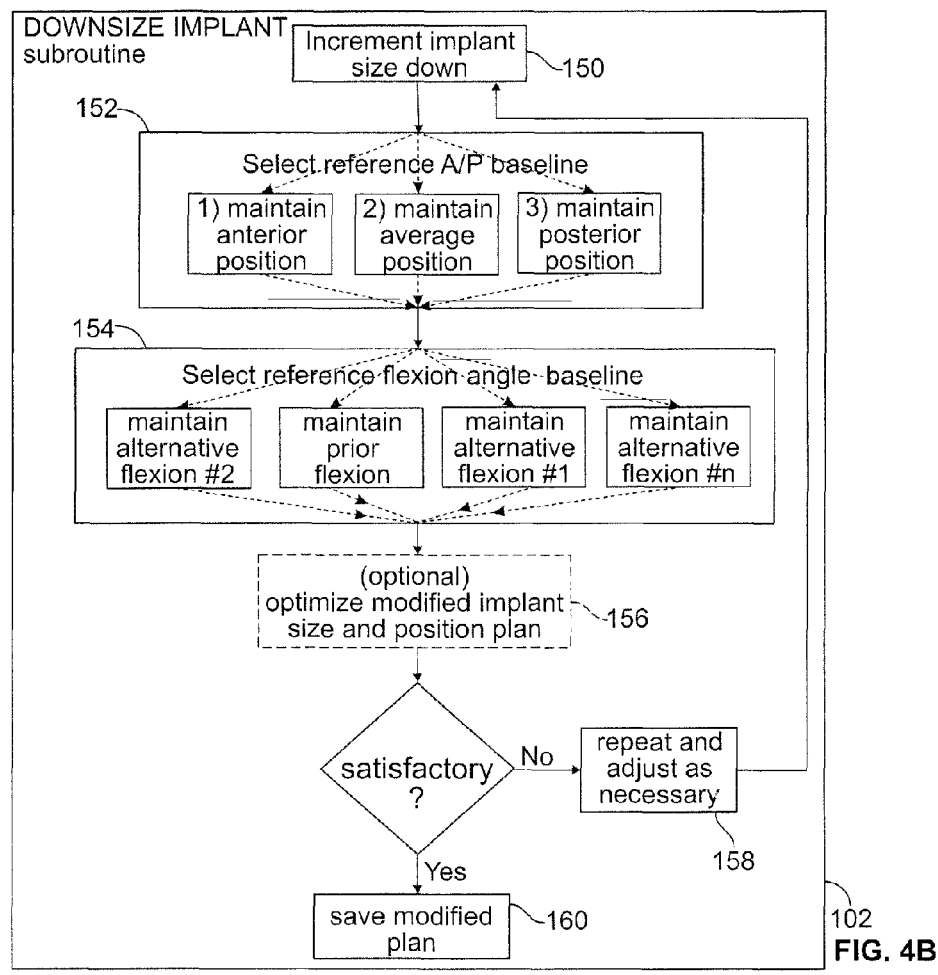
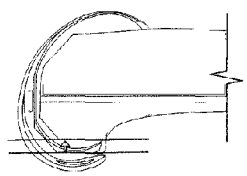
"Keep Anterior" moves the posterior resection plane for one size.
FIG. 6A
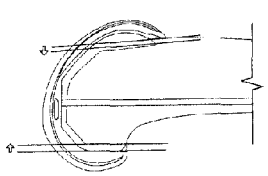
"Keep Average" moves anterior and posterior plane for a half size.
FIG. 6B
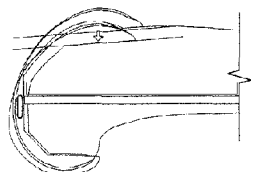
"Keep Posterior" moves the anterior resection plane for one size.
FIG. 6C

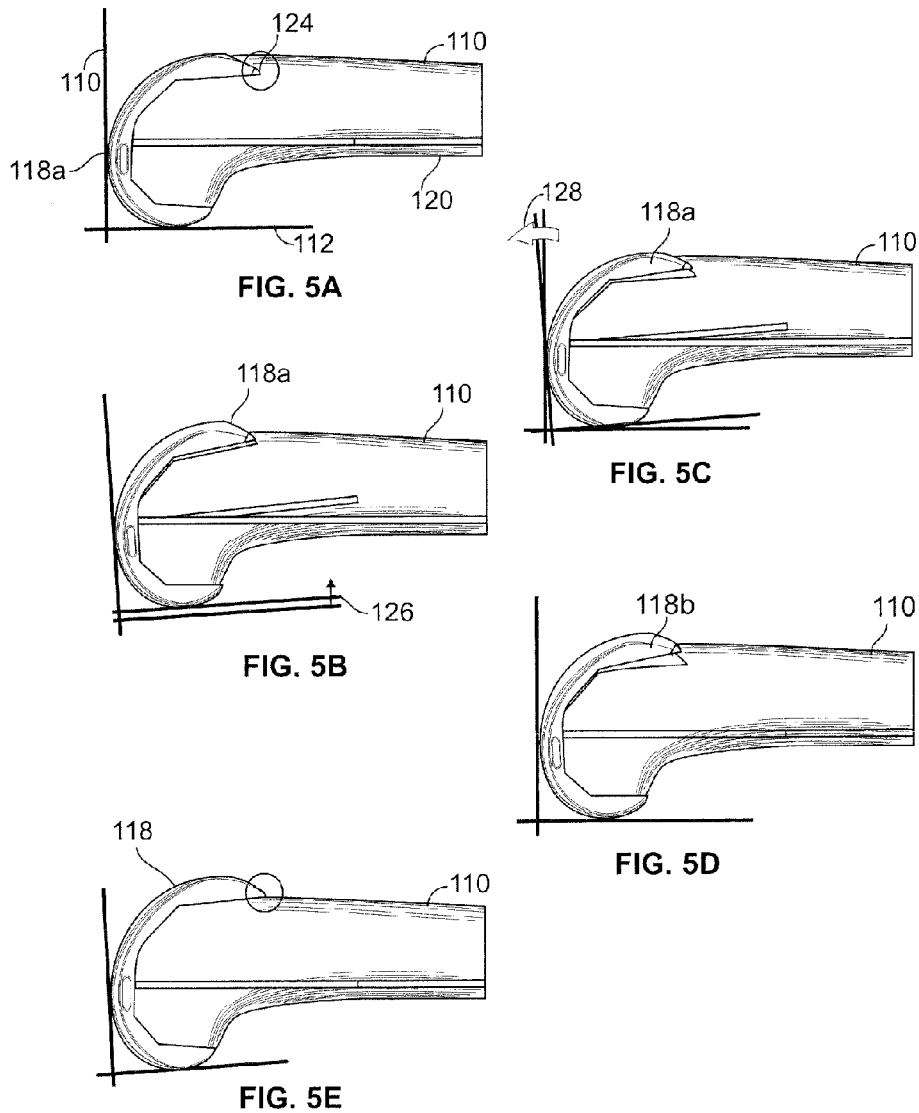

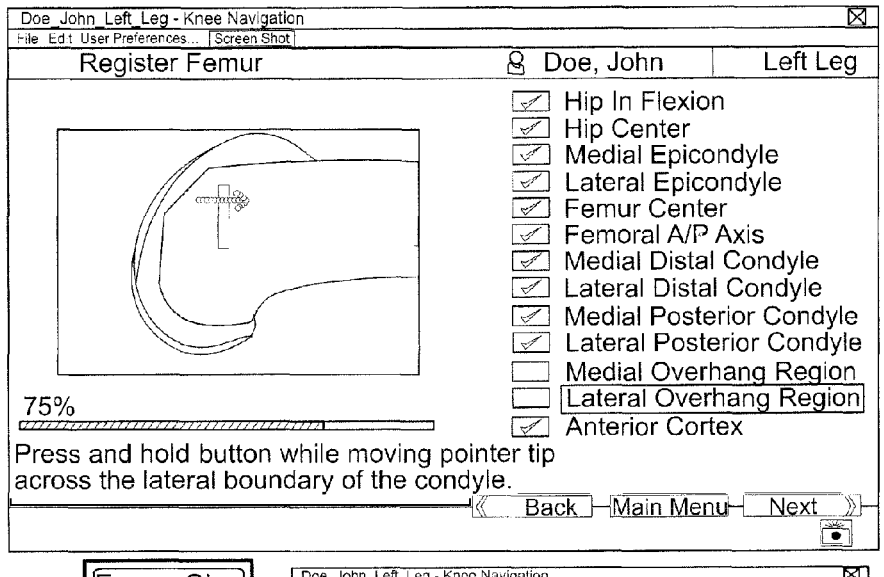
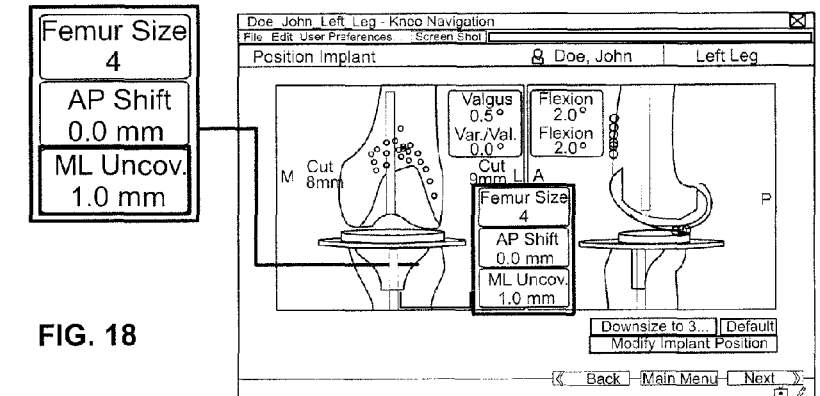
FIG. 18
Detect ML Overhang
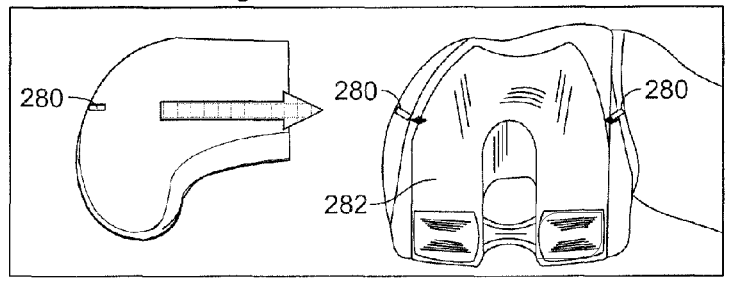
FIG. 19

US 8,617,173 B2

SYSTEM FOR ASSESSING A FIT OF A FEMORAL IMPLANT

CROSS REFERENCE TO RELATED APPLICATIONS

This application is a divisional of, and claims priority to, U.S. patent application Ser. No. 12/221,858 filed on Aug. 6, 2008, which claims the benefit of U.S. Provisional Patent Application No. 60/963,738, filed Aug. 7, 2007, and claims the benefit of U.S. Patent Provisional Application No. 60/963,916, filed Aug. 8, 2007, each of which is incorporated by reference herein in its entirety.

REFERENCE REGARDING FEDERALLY SPONSORED RESEARCH OR DEVELOPMENT

Not applicable

SEQUENTIAL LISTING

Not applicable

BACKGROUND

1. Field of the Disclosure

The present disclosure relates generally to a method of and system for planning a surgery, such as selecting a size and position for an orthopedic prosthesis implant.

2. Background

Computer aided surgical systems for orthopedic and/or arthroplasty procedures are useful for both planning and executing various procedures. One known system and method is described in U.S. patent application Ser. No. 11/290,039, filed Nov. 30, 2005, which is incorporated by reference in its entirety herein. Another known system and method is described in U.S. patent application Ser. No. 10/961,455, filed Oct. 8, 2004, and published as U.S. Patent Application Publication No. 2006/0095047, which is incorporated herein by reference in its entirety.

As diagrammatically shown in FIG. 1, a total knee arthroplasty surgical procedure includes removing affected sections of a distal end of a femur 10, including lateral condyle 12 and medial condyle 14, and an opposing proximal end of a tibia 16 and replacing the removed bone portions with prostheses, including a femoral implant 18 for attachment to a the femur and a tibial implant 20, which includes a base plate 22 for attachment to the tibia and an articular surface 24. To accomplish this, a surgeon resects the condyles at the distal end of the femur to have a shape (shown in dashed lines) complementary to an inner surface 26 of the femoral implant 18 in order to accept the femoral implant thereon. The surgeon also resects the proximal end of the opposing tibia 16 in a shape (shown in phantom dashed lines) to complementarily receive the base plate 22 thereon. The femoral implant 18 and the base plate 22 are secured, such as with adhesive or fasteners, to the respective bones 10 and 16, and the articular surface 24 is secured to the base plate facing the femoral implant. After the patella (not shown for clarity) and soft tissues, including tendons and muscles (not shown for clarity), are properly repositioned around the knee, the femoral implant 18 is able to articulate on the articular surface 24 in a manner resembling natural knee motion.

A navigation system may be used to obtain data during the total knee replacement procedure in order to create a map of relevant portions of the patient, such as the femur 10, femoral condyles 12 and 14, tibia 16 and tibial plateau, fibula, and patella, which may then be displayed on a display, such as a video or computer monitor. One possible mapping system may use, for example, a navigation system as disclosed in Patent Application Publication No. 2001/0034530, in conjunction with a tracking device as disclosed in U.S. Patent Application Publication No. 2005/0199250, published Sep. 15, 2005, each of which is incorporated by reference herein in its entirety. In other possible systems, the mapping data may be obtained by other known pre-operative and/or intra-operative techniques. Using the map, a surgeon is then able to virtually plan the remaining steps of the procedure, including choosing a particular size and/or shape of a replacement prosthesis, and then virtually laying out resections in order to obtain a desired final fit and location of the prosthesis on the remaining bone. This step may be performed using a database of known prosthesis shapes and/or sizes that are then compared to the acquired map data and shown juxtaposed and/or superimposed therewith on the display monitor. After the procedure has been fully planned using the map and prosthesis form factor data, the navigation system may be used to track the physical steps of the operation, such as making the various resections so that the surgeon may advance through the procedure according to the plan. In other methods, steps for executing the plan of the operation may be performed without the aid of a virtual navigation system using other known layout techniques.

The steps of choosing a particular prosthesis and choosing a preferred layout of the prosthesis on the existing bone have, until now, been dependent wholly or in large part on the skill and experience of the person planning the procedure, such as the surgeon. For example, in a method of visually choosing and adjusting the prosthesis, after obtaining the map of the relevant bones, the surgeon would manually choose a specific size of prosthesis based on his or her experience in visual comparison to the map of the bone. The surgeon—after indicating to the computer which prosthesis was being used—would then visually adjust the position of the prosthesis in comparison with the shape of the appropriate bone (as shown virtually superimposed together on the display screen) by trial and error until a desired position was chosen. The surgeon would then cause the computer to record the chosen position in relation to the map and then use that information to guide the remaining steps of the procedure. Other techniques may simply select a prosthesis size and position based on a single parameter, such as minimizing or eliminating any steps, or notches, in a resected surface of the bone, which may cause localized stress concentration points where premature failure may be more likely to occur.

The method of visually choosing and adjusting the prosthesis can give rise to certain challenges. One challenge—choosing the correct size of prosthesis—is limited by the ability of the surgeon to choose the correct size based solely on the map information of the bones. Another challenge—positioning the prosthesis in the best arrangement with respect to the bone—is limited by both by the size of the prosthesis chosen by the surgeon and the ability of the surgeon to visualize the optimum positional arrangement. A detriment to choosing a non-optimal position and/or size of the prosthesis may be the creation of a notch or an area where the edge of the prosthesis and the surface of the bone do not align well and require an undesirably large runout of the resected portion of the bone beyond an end of the prosthesis or a large overhang or gap between the end of the prosthesis and uncut portions of the bone. A major constraint on the ability of the surgeon to most efficiently plan the procedure is that time is of the essence during a surgical procedure in order to minimize the time during which the patient is incised, and, often, planning can only be initiated and/or completed after the patient has been incised.

Therefore, it would be desirable to have a system and method that will facilitate more accurate and time efficient planning of the procedure to help ensure that an optimal size and position of the prosthesis is planned in order to prevent or minimize the creation of notches in the bone and other inefficiencies and/or less desirable design alternatives.

SUMMARY OF THE INVENTION

In one embodiment of the invention, a system for assessing a fit of a femoral implant to a distal end of a femur in a selected orientation prior to resecting the femur includes means for obtaining pre-defined form factor information for plurality of femoral implants and means for obtaining surface shape information of the distal end of the femur. The system further includes means for automatically performing a virtual fit assessment of each possible incremental position of a pre-defined set of incremental positions for each size implant to be considered prior to resecting the femur and means for selecting an optimal implant size and position from the virtual fit assessments.

In another embodiment of the invention, a system for virtually planning a size and position of a prosthetic implant for a bone on a patient includes a database containing pre-defined form factor information for a plurality of different implants and a circuit for obtaining surface shape information of the bone. The system further includes a circuit for defining baseline location parameters for an implant location in relation to a virtual representation of the bone based on the surface shape information and a circuit for assessing a fit calculation of each implant in relation to the virtual representation of the bone based on the form factor in formation and a plurality of fit factors at each of a plurality of incremental positions in relation to the bone. Still further, the system includes a circuit for selecting a best fit implant size and position from all of the fit calculations.

In yet another embodiment of the invention, a computer readable medium for automatically virtually calculating an optimum size and position of a prosthetic implant for a bone includes a first routine for obtaining pre-defined form factor information for a plurality of different implant sizes and a second routine for obtaining surface shape information of the bone. A third routine defines baseline location parameters for an implant location in relation to a virtual representation of the bone. A fourth routine for assesses a fit calculation for each implant in relation to the virtual representation of the bone based on a plurality of fit criteria at each of a plurality of incremental positions in relation to the bone. A fifth routine selects an optimal implant size and position from each fit assessment based on a weighted comparison of each fit calculation for each of the plurality of fit criteria.

In a further embodiment of the invention, a method of virtually planning a size and position of a prosthetic implant for a bone on a patient includes the steps of obtaining pre-defined form factor information for a plurality of different implants, obtaining surface shape information of the bone, defining baseline location parameters for an implant location in relation to a virtual representation of the bone, assessing a fit calculation of each implant in relation to the virtual representation of the bone based on a plurality of fit factors at each of a plurality of incremental positions in relation to the bone, and selecting a best fit implant and position from all of the fit calculations.

In still a further embodiment of the invention, a method of assessing a fit of a femoral implant to a distal end of a femur in a selected orientation prior to resecting the femur includes the steps obtaining pre-defined form factor information for the femoral implant, obtaining surface shape information of the distal end of the femur, and performing a virtual fit assessment at each of all possible incremental positions of a pre-defined set of incremental positions for each size implant to be considered prior to resecting the femur.

BRIEF DESCRIPTION OF THE DRAWINGS

FIG. 4B is a flow diagram of a still further aspect of the present disclosure;

FIGS. 5A-5E are diagrammatic representations of steps shown in FIG. 4A;

FIGS. 6A-6C are diagrammatic representations of options shown in FIG. 4B;

FIG. 18 shows screen shots of a register femur feature of the system;

FIG. 19 is another diagrammatic view of a distal end of a femur showing medial/lateral implant overhang;

DETAILED DESCRIPTION

Figure 2:
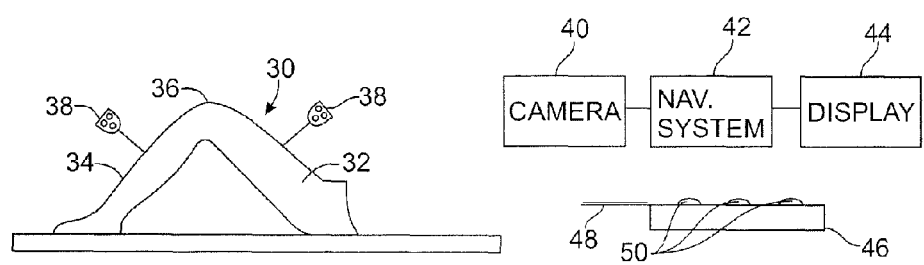
FIG. 2 is a schematic view of a patient's knee that has been prepared for knee replacement surgery using components of one embodiment of a surgical navigation system.

As diagrammatically shown in FIG. 2, a patient's leg 30 may be prepared for knee replacement surgery with the leg 30 bent so that the patient's upper leg or femur 32 is at an angle of approximately 90 degrees to the patent's lower leg or tibia 34. This positioning of the leg 30 places the patient's knee 36 in position for the procedure. Two tracking devices 38 that can communicate with a camera 40 associated with a computer assisted surgical navigation system 42 are associated with the femur 32 and the tibia 34 such that the tracking devices 38 move with the femur 32 and the tibia 34, respectively. The association can be by direct attachment to the respective bones or by other possible association methods. The computer assisted surgical navigation system 42 is, in one embodiment, one that is well known in the art and will not be further discussed here. Suitable surgical navigation systems 42 are described in U.S. Patent Publication No. 2001/0034530. A typical navigation system 42 will also include a display device 44, such as a computer or video monitor. In addition, most navigation systems 42 will also use specialized tools, such as a pointer 46 that has been previously calibrated to work with the navigation system 42. The calibration of the pointer 46 enables the navigation system 42 to determine the precise location of a pointer tip 48 by locating a series of locator devices 50 such as LED's located on the pointer 46. These locator devices 50 are, in one embodiment, the same type used for the tracking devices 38.

Figure 3:
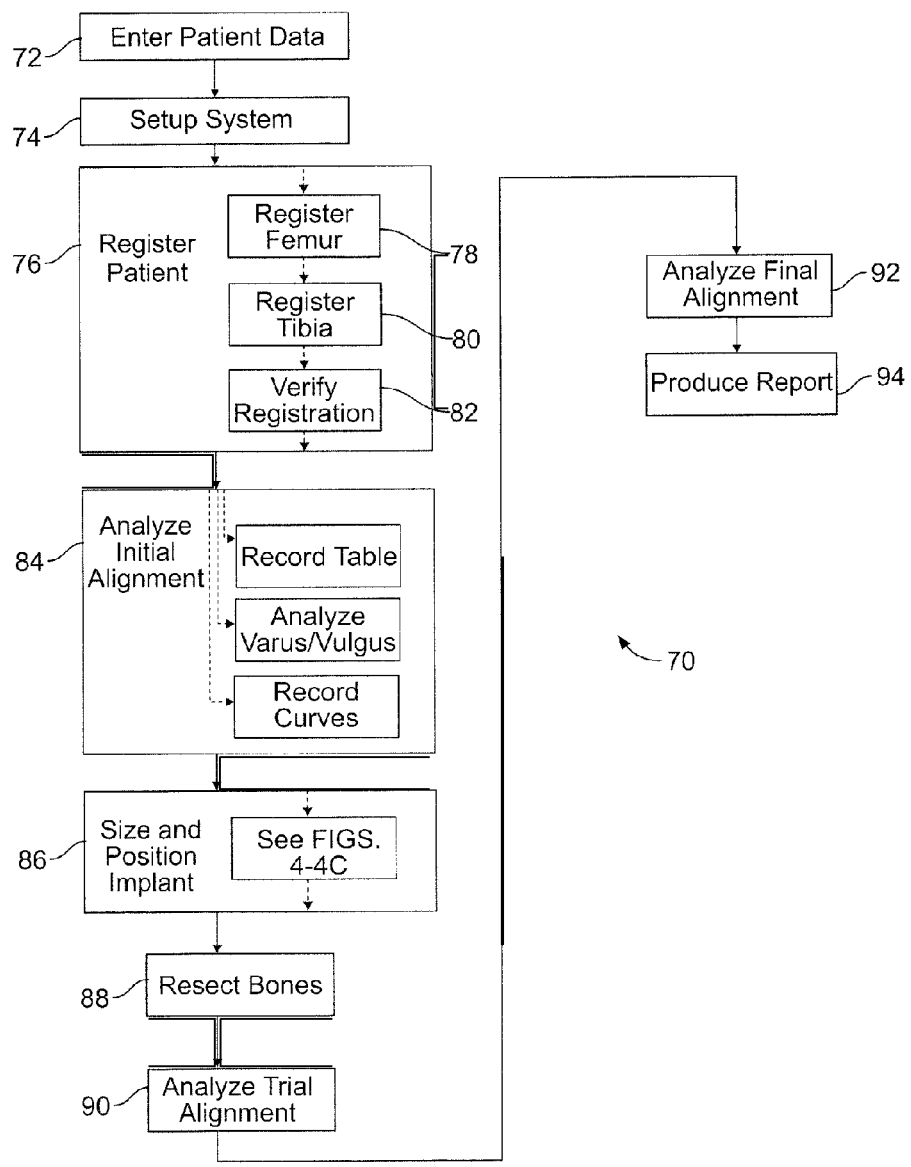
FIG. 3 is a flow diagram of one aspect of the present disclosure.

FIG. 3 illustrates one embodiment of a method 70 of performing a prosthesis implant surgical procedure. The method 70, in one embodiment, is adapted to be implemented using the computer aided navigation system 42, which both guides step-by-step planning and execution of the surgical procedure, as disclosed in detail herein-below. However, the method 70 is not limited to use with any particular implementation system and also may be adapted for use and/or implementation with other systems capable of performing the steps of the method. For purposes of example only, the method and system of the present disclosure is described in conjunction with planning and executing a total knee arthroplasty or total knee replacement surgical procedure. However, it is understood that the method and system may be applied to other surgical procedures with minor modifications without departing from the spirit of this detailed example.

In one embodiment, the method 70 begins with the step of creating a patient file, which in one embodiment is in computer readable form, and entering data for preselected parameters, such as patient name, date, surgical procedure, etc. with an enter patient data routine 72. Next, a navigation system, such as the navigation system 42, is set up, which may include the step validating the position of a pointer such as the pointer 46, with a setup system routine 74. After validation, the location of the patient is registered with the navigation system, such as by the using the pointer, with a register patient routine 76, which in one embodiment includes a defining verification points subroutine, a register femur subroutine 78, a register tibia subroutine 80, confirming which side leg is being operated on, and a verify registration subroutine 82. During the register femur subroutine 78, a detailed survey is performed of the relevant surfaces of the femur, including at least the anterior cortex, and the most proximal, distal, medial, and lateral points of the lateral and medial condyles using appropriate survey instruments, as described in additional detail hereinafter. Similarly, a survey is performed of the relevant surfaces of the tibia during the register tibia subroutine 80. Data regarding other relevant biomechanical properties of the patient, such as the kinematics of the subject joint, also may be gathered during the register patient routine 76, by direct observation and/or interpolation. Data from the surveys are then processed by the computer to generate a virtual image or map of the surveyed surfaces for display on the display screen and for use throughout the remaining steps of the surgical procedure 70. After registering the patient with the navigation system, the surgeon may then analyze relevant biomechanical properties of the subject area, such as the pre-operative alignment of the knee, with an analyze initial alignment routine 84. During the analyze initial alignment routine, the surgeon may, in one embodiment, record a table, analyze varus/valgus angles of the knee, and/or record curves. The information gathered from the register patient routine 76 and analyze initial alignment routine 84 is used in a size and position implant routine 86 to obtain a final implant size and position plan in a new manner, as described in detail hereinafter. The final implant size and position plan may then be used for directing and/or providing guidance for remaining steps in the surgical procedure, such as resecting the bones during a resect bone routine 88, attaching and analyzing a trial alignment of trial prostheses during an analyze trial alignment routine 90, attaching and analyzing a final alignment of final prostheses during an analyze final alignment routine 92, and producing a report of the procedure during a show report routine 94 according to well known surgical navigational techniques and computer aided data processing techniques.

Figure 4:
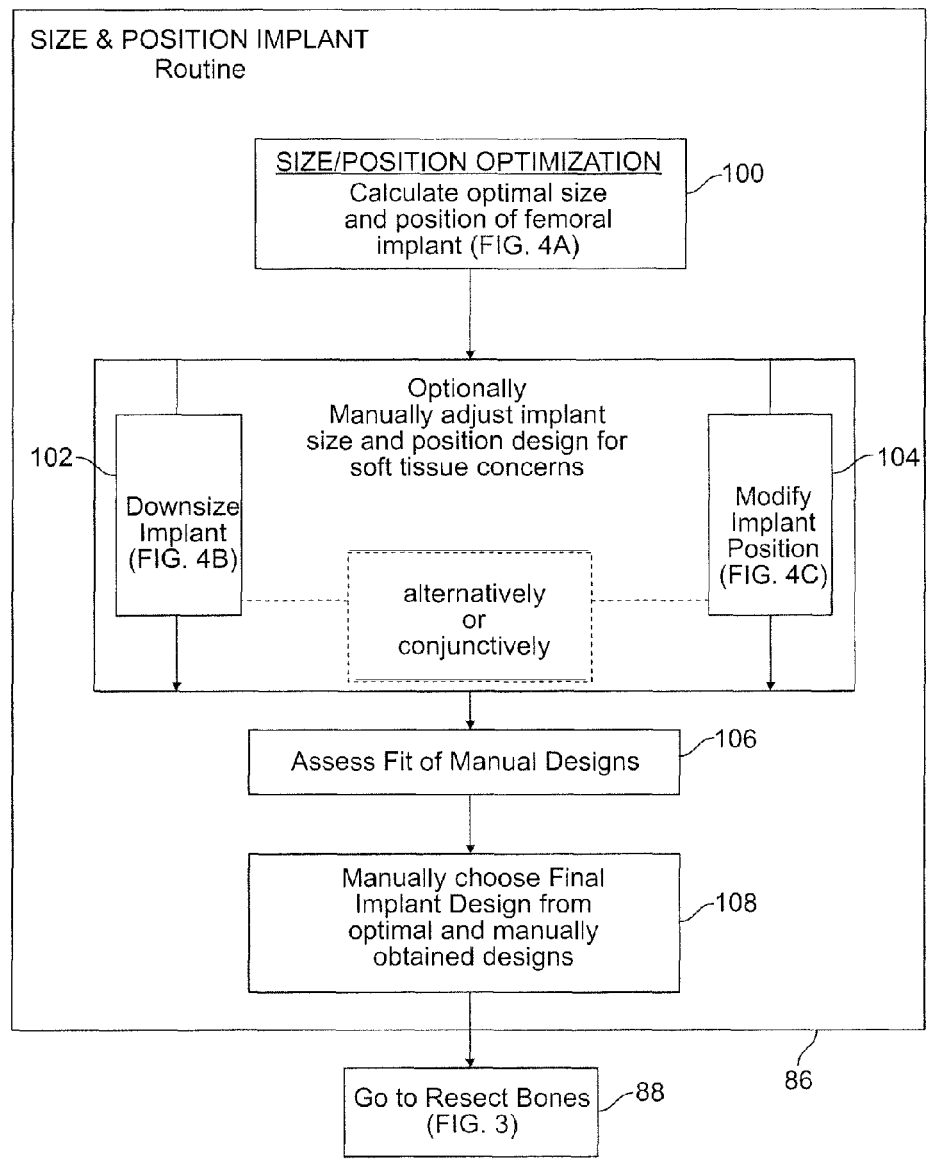
FIG. 4 is a flow diagram of another aspect of the present disclosure.
Figure 4A:
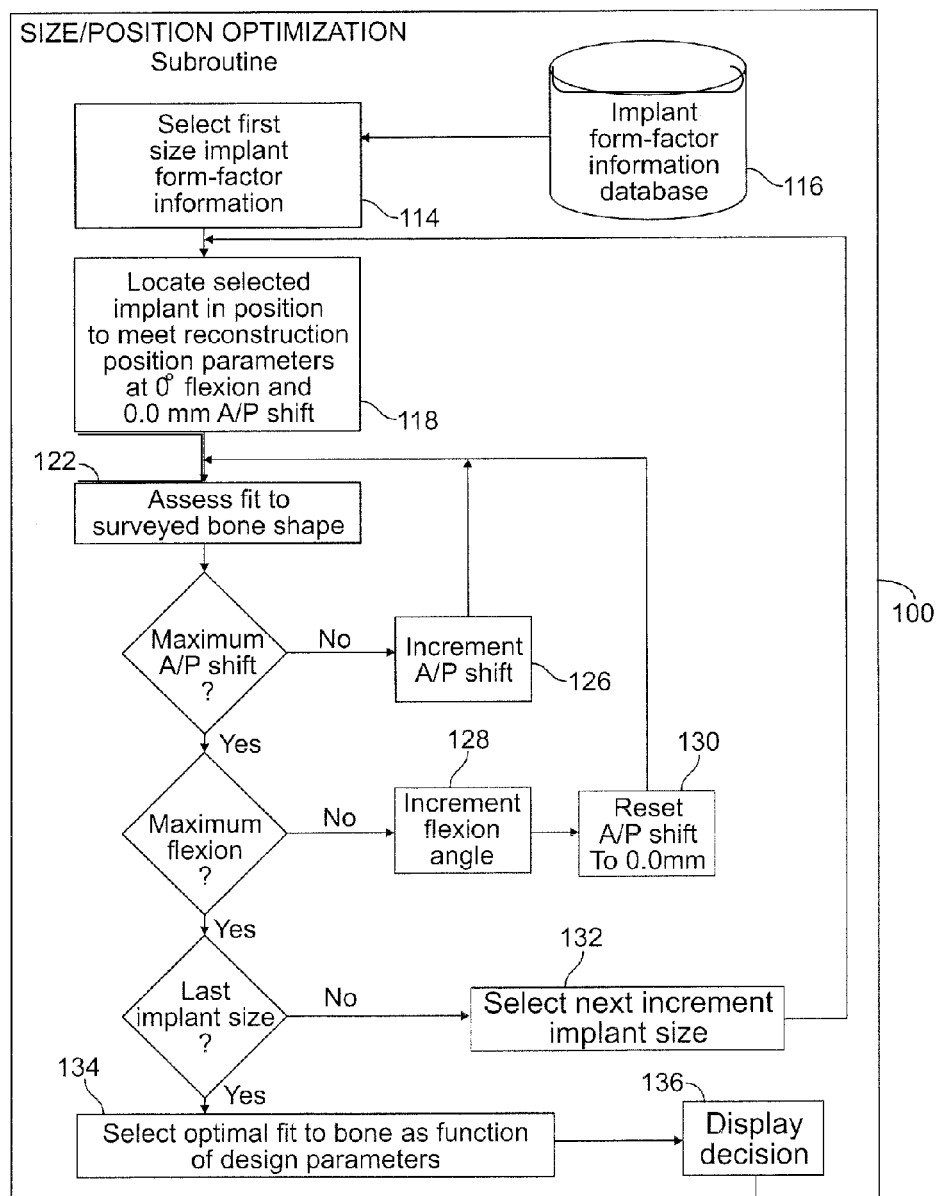
FIG. 4A is a flow diagram of a further aspect of the present disclosure.

Turning now to FIGS. 4-6C, one embodiment of the size and position implant routine 86 is disclosed, during which an optimal implant size and position plan, including optimal size and position of a specified femoral implant type, is automatically calculated by assessing a plurality of fit parameters for each possible combination of a range of possible sizes and a range of possible positions based on a set of prioritized parameters using an automatic size/position optimization subroutine 100. In one embodiment, the automatic size/position optimization subroutine 100 automatically selects an optimal size femoral implant and attachment position of the femoral implant to the distal end of the femur in a manner, as shown schematically in detail in FIG. 4A, that only considers rigid bone shape and femoral implant shape parameters and does not take into account any soft tissue or other anatomical conditions, such as size and gender of the patient, that may also affect a final size and position plan for the prostheses which will be used by the surgeon to actually attach the implants to the patient. Therefore, the automatically calculated optimal implant size and position plan subsequently may be adjusted manually as deemed necessary by the surgeon, with appropriate input from the surgeon, in one or both of a downsize implant subroutine 102 (FIG. 4B) and a modify implant position subroutine 104 (FIG. 4C) to produce one or more adjusted implant size and position plans. The adjusted implant size and position plans, in one embodiment, are assessed for fit to the bone by the surgeon. The surgeon then chooses the final implant size and position plan for executing the remaining steps of the surgical procedure from all the prior plans considered in a step 108 based on his or her knowledge and experience.

In one embodiment of the automatic size/position optimization subroutine 100 shown in detail in FIGS. 4A and 5A-5E, a preselected set of calculations automatically sequentially assesses the fit of each size femoral prosthesis—such as from smallest to largest—with the shape of the bone at each position having two degrees of freedom for four prioritized fit criteria. In one embodiment for fitting a femoral implant to a distal end of the femur, the four prioritized fit criteria include: the maximum run out of the anterior resection from the proximal end contour of the anterior portion of the implant, percentage of the proximal end contour of the anterior portion of the implant that lies on cut bone, percentage of the proximal end contour of the anterior portion of the implant that lies on or above uncut anterior cortex bone, and the maximum gap between the implant and the uncut surface of the anterior cortex. For example, the first criteria may be that the run out must not be more than 12 mm. The second criteria may be that a minimum of 60% of the proximal end contour of the anterior portion of the implant lies on cut bone. The third criteria may be that a minimum of 1% of the proximal end contour of the anterior portion of the implant lies on or above uncut anterior cortex bone. The fourth criteria may be that the maximum gap between the proximal implant contour and the uncut anterior cortex is preferably smaller than 1.5 mm. A notch is calculated to be present if either the maximum run out is larger than 12 mm or the entire proximal end contour of the anterior portion of the implant is lying on resected anterior cortex bone. In one embodiment, the preselected set of calculations is performed electronically by the computer that runs the navigation system 42, and the calculations are based on the survey data obtained during the register patient routine 76 and a pre-loaded database including form factor information for a pre-selected group of prostheses of one or more types of prostheses and for each of a plurality of sizes of each type of prosthesis, which is accessible by the computer, such as from an electronic memory system. In other embodiments, the preselected set of calculations is performed by a different electronic computer and/or by other computing machines and/or by human effort, and the survey data is obtained by other methods capable of providing the necessary anatomical information regarding the subject bones. The surgeon, in one embodiment, selects a type of prosthesis based on other factors and the computer then assesses the fit for each size and position of the selected type as described immediately hereafter.

Prior to initiating the automatic size/position optimization subroutine 100, the surgeon may first define a target reconstruction position based on design parameters for matching a selected varus/valgus angle, rotation angle, and/or surface position of the posterior condyles and distal condyles. As shown diagrammatically in FIG. 5A, the reconstruction position defines a design base line 110 for the distal condyle surfaces and a design base line 112 for the posterior condyle surfaces, which are the surfaces that the surgeon initially hopes to maintain constant in the final implant size and position plan. With the surface of the reconstructed distal and posterior condyles having been set, in a first step 114 of one embodiment, a first size implant 118a, such as a smallest size, is selected and form factor information therefor is retrieved from an implant form factor database 116. In a step 118, the first size implant 118a is located to the map of the femur 10 with the distal condyle position and posterior condyle position maintained at all times at the reconstructed design base lines 110 and 112. The step 118 locates the first size implant 118a at a default position of 0° flexion and 0.0 mm anterior/posterior shift (A/P shift) with reference to a mechanical axis 120 of the femur 10. The fit of the first size implant 118a is assessed during a step 122 using the above-identified four criteria to assess at least notching, as shown at 124 in FIG. 5A. If the A/P shift is not the maximum A/P shift for the current flexion angle, the A/P shift is incremented anteriorly at step 126, such as by 0.5 mm in one embodiment shown diagrammatically in FIG. 5B, and the fit is assessed at this new position at step 122. This cycle of steps 122 and 126 is repeated until the maximum A/P shift is assessed at a given flexion angle, after which the flexion angle is incremented at a step 128, shown diagrammatically in FIG. 5C, the A/P shift is reset to the default position at step 130, and the fit of the new flexion angle is assessed at step 122. The steps of 122, 126, 128, and 130 are repeated until the fit for each position corresponding to all the possible pairs of flexion angle and A/P shifts for the first size implant 118a have been calculated. In one embodiment, the assessed flexion angles range in 1° increments from 0° to a maximum of 5° and the assessed A/P shift ranges in 0.5 mm increments from 0.0 mm to a first increment that is calculated to overlap with the next size implant increment and/or until no notch is formed in the anterior cortex of the bone. Preferably, the implant is flexed around a single radius of the implant to assure that the reconstructed distal and posterior condyles are maintained at the respective base line positions. After the fit has been assessed at all the positions of the first size implant 118a, the next size implant increment 188b is selected at step 132, as shown diagrammatically in FIG. 5D, and the steps 122, 126, 128, and 130 are repeated in similar manner. The steps 122, 126, 128, 130, and 132 are repeated in like manner for each successive increment size implant in the database until all of the implant sizes for the selected implant type have been fully assessed at each possible incremental position for both the A/P shift and flexion degrees of freedom. After the fit of each size implant has been fully assessed, all of the assessed fits are compared with a weighted algorithm during a step 134 to identify an automatic optimal size and position plan from all the assessed sizes and positions that at least minimizes or eliminates any notching of the bone and over sizing of the implant. At a step 136, an image of the femoral implant is then superimposed over an image of the femur in the automatic optimal implant size and position plan for use in further steps, as shown diagrammatically at FIG. 5E. In other embodiments, the steps for advancing through all of the possible sizes and positions to obtain fit assessments at each possible position for each possible size may be taken in different orders than described herein, preferably as long as a fit assessment is taken all of the possible incremental positions for each size implant to be considered.

As shown schematically in FIGS. 4B and 6A-6C, after the optimal implant size and position plan is calculated, the surgeon may choose optionally to manually modify the size and position, such as to make adjustments to allow for soft tissue or other anatomical considerations, in the downsize implant subroutine 102. In a step 150, the surgeon selects the next incrementally smaller size femoral implant than the automatically calculated optimal size. With the new implant size, at a step 152 the surgeon selects between three alternative options of a baseline A/P shift that is to be maintained: 1) maintaining the anterior position of the implant at downsizing, shown diagrammatically in FIG. 6A, 2) maintaining the anterior-posterior center of the implant at downsizing, shown diagrammatically in FIG. 6B, and 3) maintaining the posterior position of the implant at downsizing, shown diagrammatically in FIG. 6C. The surgeon also selects a baseline flexion angle to maintain in a pre-set range, such as between 0° and 5°, by selecting to either maintain the previous flexion angle or selecting one of the remaining angle choices. The fit of the new implant size is then assessed in the same manner as previously described and a resulting modified size and position plan is produced. The surgeon may choose to repeat and adjust the modified implant size and position plan at a step 158 based on his or her inspection and knowledge and experience until the surgeon believes that the best size and position has been found to take into account soft tissue considerations. Once a satisfactory modified implant size and position plan is identified, the identified plan may is saved for future use at a step 160.

Figure 4C:
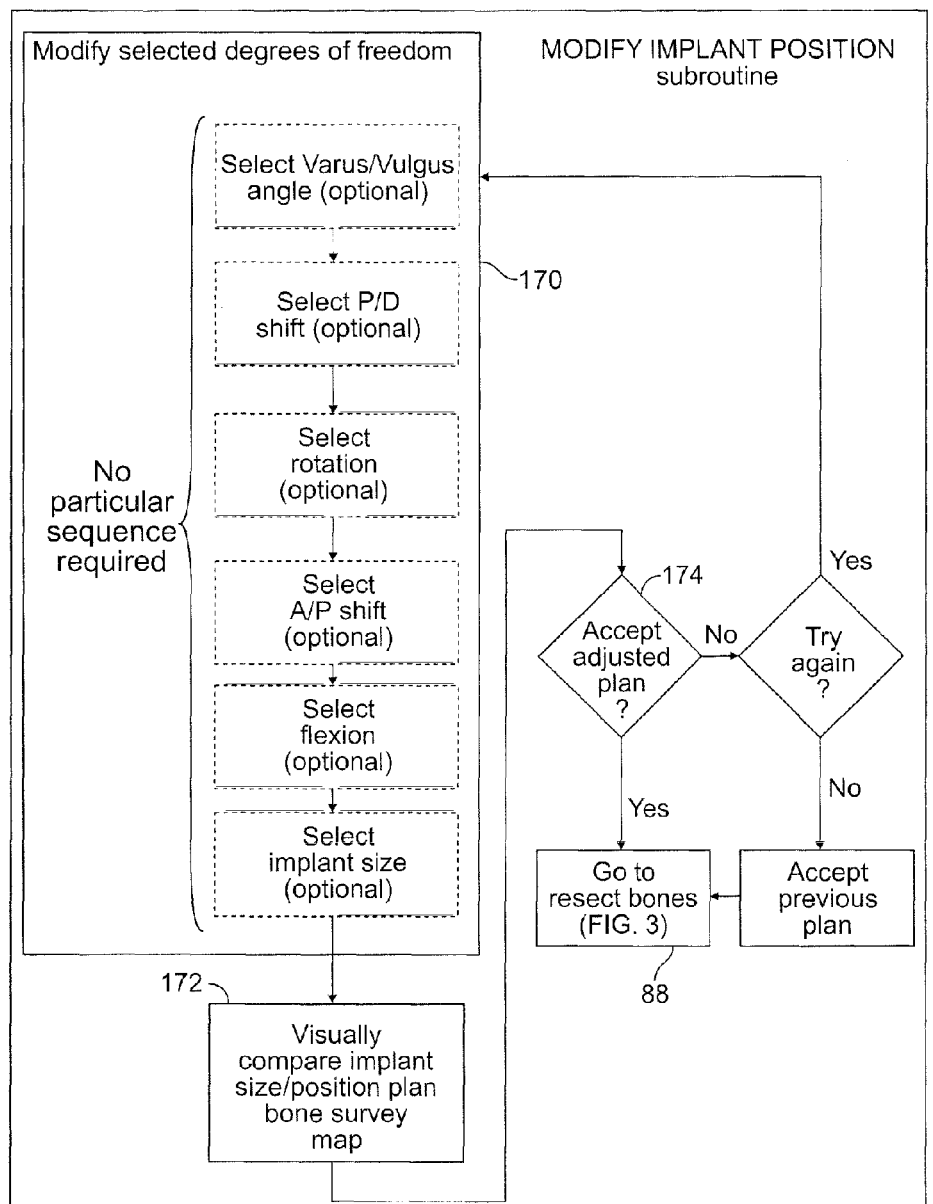
FIG. 4C is a flow diagram of a yet additional aspect of the present disclosure.
Figure 7:
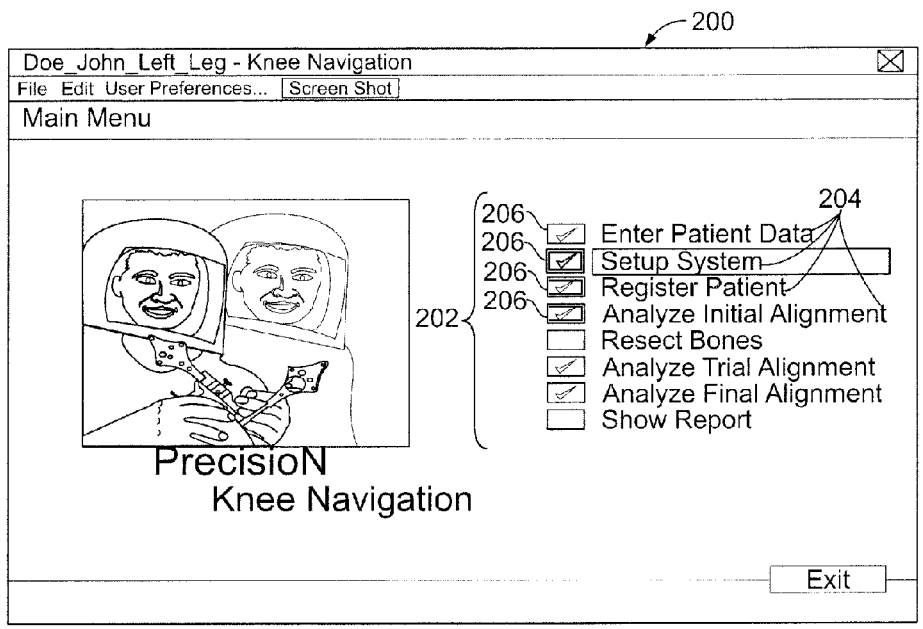
FIG. 7 is a screen shot showing one aspect of a main navigation menu of a system of the present disclosure.

In the modify implant position subroutine 104, shown schematically in FIG. 4C, the surgeon also may choose optionally to, in addition or alternatively to the downsize implant subroutine 102, directly modify all of the available degrees of freedom set in the automatically optimized implant size and position plan and/or the modified implant size and position plan at will in a step 170, including the varus/valgus angle, the proximal/distal shift distance, the rotation angle, the A/P shift distance, flexion angle, and the implant size as desired based on the knowledge and experience of the surgeon in order to make necessary adjustments for soft tissue and/or other anatomical considerations. Such manual modification may allow the surgeon to quickly bypass clearly unnecessary size and position iterations and/or provide a user override, such as based on the knowledge and experience of the surgeon. At a step 172, the fit of the modified implant size and position plan is assessed from step 170 and the surgeon visually analyzes the modified implant size and position plan and decides at a step 174 whether to accept such plan, at a step 176 whether to try more modifications, and/or at a step 178 whether to accept the previous plan. In one embodiment, fit is assessed at each manually selected position for both the downsize implant subroutine 102 and the modify implant position subroutine 104 in order to identify whether a particular implant size and position plan will create a notch in the anterior cortex if either the maximum run out is more than 12 mm or the entire proximal implant contour is lying on a cut surface of the anterior cortex bone, which allows the surgeon to choose to either accept or reject each manually selected position based on his or her experience and knowledge.

At the end of any one of the subroutines 100, 102, and 104, the surgeon may elect to advance to the resect bones subroutine 88 after selecting a final implant size and position plan to be used for guiding the remaining steps of the surgery from any of the plans considered. After performing the above steps, the surgeon selects the final implant size and position plan, either from the original automatically calculated optimal implant size and position plan or from any of the modified implant size and position plans. Of course, the surgeon may simply choose to omit the manual adjustment and choose to rely on the automatically calculated optimal size and position.

Figure 1:
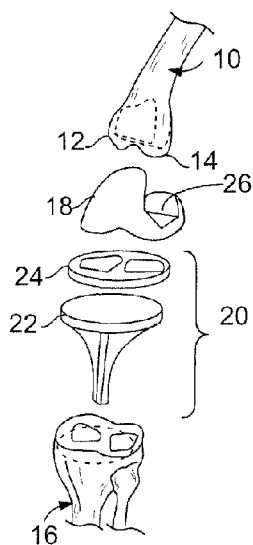
FIG. 1 is an exploded partial diagrammatic view of knee bones and prostheses involved in a total knee arthroplasty.

FIGS. 7-13 show one embodiment of a computerized system for implementing the above-described method of FIGS. 3-6C in conjunction with the hardware shown in FIG. 2 to install a total knee replacement as shown in FIG. 1. Software for implementing the above-described method drives a computer, such as the navigation computer 112, which also has access to the survey and map data of the bones of interest and to the implant form factor information database 116. A main menu screen 200, shown in FIG. 7, displays a main menu 202 that can help guide the surgeon through the surgical procedure. The main menu 202 includes buttons 204 for initiating each of the following routines as previously described herein: the enter patient data routine 72, the setup system routine 74, the register patient routine 76, the analyze initial alignment routine 84, the position implant routine 86, the resect bones routine 88, the analyze trial alignment routine 90, the analyze final alignment routine 92, and the show report routine 94. A visual indication, such as a check mark 206, is associated with each button to indicate whether the routine has been completed, thereby providing a visual cue to help guide the surgeon through the procedure.

Figure 8:
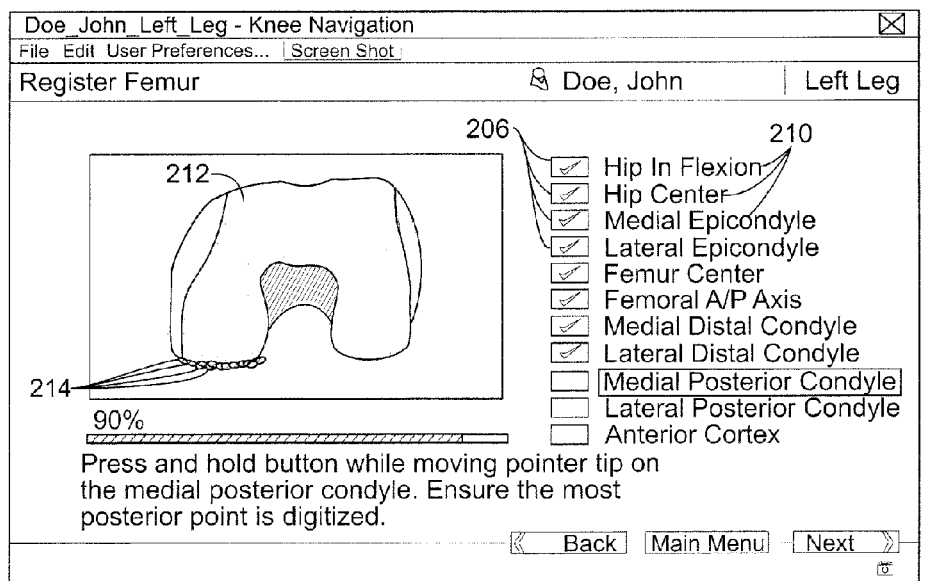
FIG. 8 is a screen shot showing one aspect of a bone mapping feature of the system.
Figure 9:
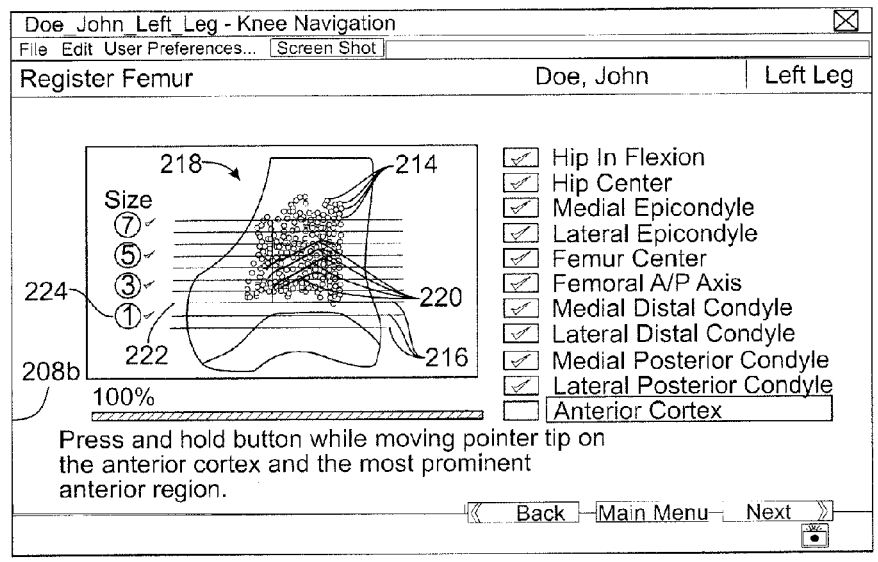
FIG. 9 is a screen shot showing an aspect of another bone mapping feature of the system.

As shown in FIGS. 8 and 9, selecting the button 204 associated with the register patient data routine 76 from the main menu screen 200 displays one of various register patient screen 208a, 208b that display subroutine buttons 210 for performing each of various patient registration steps, including a hip in flexion registration subroutine, a hip center registration subroutine, a medial epicondyle registration subroutine, a lateral epicondyle registration subroutine, a femur center registration subroutine, a femoral A/P registration subroutine, a medial distal condyle registration subroutine, a lateral distal condyle registration subroutine, a medial posterior condyle registration subroutine, a lateral posterior condyle registration subroutine, and an anterior cortex registration subroutine. In a similar manner as on the main menu screen 200, a visual indicator 206 is associated with each subroutine button 210 and indicates whether each subroutine has been completed to help visually guide the surgeon through the various registration subroutines. The register patient screen 208a corresponds with the medial posterior condyle registration subroutine, during which the most posterior surface of the medial condyle is surveyed. The register patient screen 208b corresponds with the anterior cortex registration subroutine, during which the surface of the anterior cortex of the femur is surveyed. A visual representation 212 of a general shape of the bone being resected is also displayed on the screen. The visual representation 212 is selected for each of the subroutine buttons 210 to show the particular bone being registered and mapped. For example, the posterior condyles of a femur are shown in screen 208a, and the femoral anterior cortex is shown in screen 208b. On each screen 208a and 208b, visual indications 214, such as dots, are displayed superimposed over the bone that show what survey data points have been obtained and the approximate positions thereof. In one embodiment, survey data points are acquired using a digitizer mechanism, such as the pointer 46.

Of particular interest in the register patient screen 208b shown in FIG. 9 during the anterior cortex registration subroutine, a detailed survey of the anterior cortex of the femur is performed in order to obtain an accurate map of the contours of the anterior cortex for use in the calculations performed during the position implant routine 86 described previously herein. In contour map generation, a certain amount of interpolation is generally required between observed data points in order to generate an interpolated contour map of a subject surface, as is well known in the surveying and mapping field. The accuracy of the interpolated contour map is generally directly related to the position and number of data points acquired. For example, it is generally desirable to have data points distributed in a relatively even grid and at a target density so as to form triangles between adjacent trios of data points that tend to be more equilateral than oblong and are designed to adequately represent the general topography of the subject surface. To aid the surgeon obtain a desirable set of data points during the anterior cortex registration subroutine, a digitization grid 216 is superimposed over a standardized virtual model 212 of an anterior cortex of a femur to help visually guide the surgeon in acquiring a number and location of data points to provide a contour map of the anterior cortex sufficient to meet specified design accuracy parameters. A visual indicator 214, such as a dot, is shown superimposed over the digitization grid 216 and the standardized virtual model 212 of an anterior cortex bone for each data point acquired. Another visual indicator 218 appears on the screen, such as a change in color of the grid, when a minimum number and location of data points has been acquired for meeting the design accuracy parameters. A further visual indicator, such as proximal implant contour 220 shown in yet a different color, is displayed on the screen to show the general or approximate area of specific interest that is projected to be in the general area of the interior contours of the prosthesis implant. The proximal implant contours 220 are derived from the database of implant form factor information and are determined from the registered positions of condyles and the mechanical and rotational femur axes. A still further visual indicator, such as a check mark 222 and a number 224, are displayed on the screen that show approximately what implant sizes will be adequately calculable from the data points acquired during the anterior cortex registration subroutine. Additionally, an error checking subroutine performs a mathematical interpolation to identify potentially erroneous outlier data points obtained during the anterior cortex registration subroutine, such as an air point that was not acquired on the surface of the bone. The error checking subroutine mathematically interpolates all of the acquired data points from the anterior cortex registration subroutine and computes a smoothed surface using, for example, a known spline interpolation algorithm. Data points that deviate more than a pre-specified distance from the smoothed surface are identified to the surgeon as potentially erroneous data points. The surgeon may then choose to delete or retain such points for use in creating the contour map based on his or her understanding of the surveyed surface.

Figure 10:
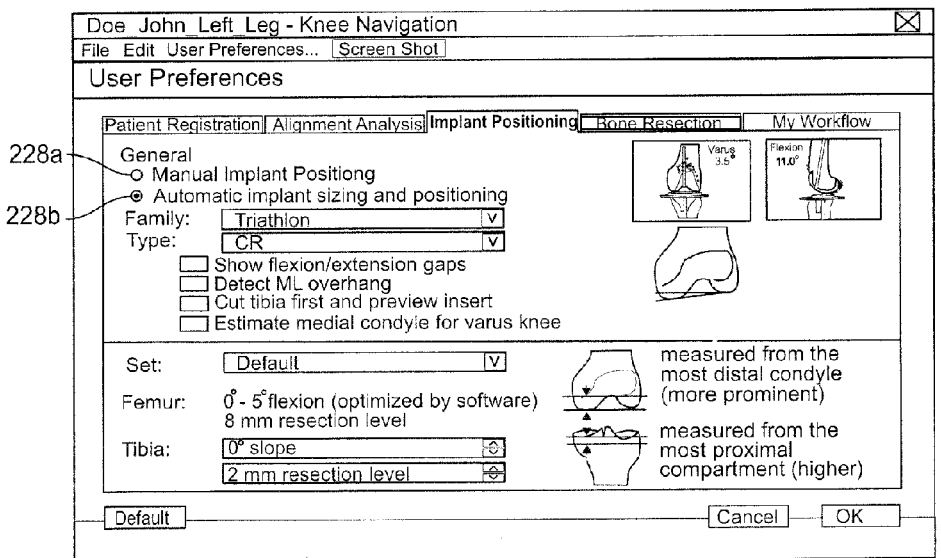
FIG. 10 is a screen shot showing an aspect of an implant positioning feature of the system.

A user preferences screen 226, shown in FIG. 10, prompts the surgeon to choose a button 228a or 228b to indicate whether to allow the surgeon to manually plan the position of the implant or whether to have the computer automatically calculate the size and position of the implant by automatically performing the automatic size/position optimization subroutine 100 after the necessary shape and biomechanical properties of the bones of interest have been retrieved. The user preferences screen 226 also allows the surgeon to set other parameters for the calculations, such as default flexion angles and resection levels.

Figure 11:
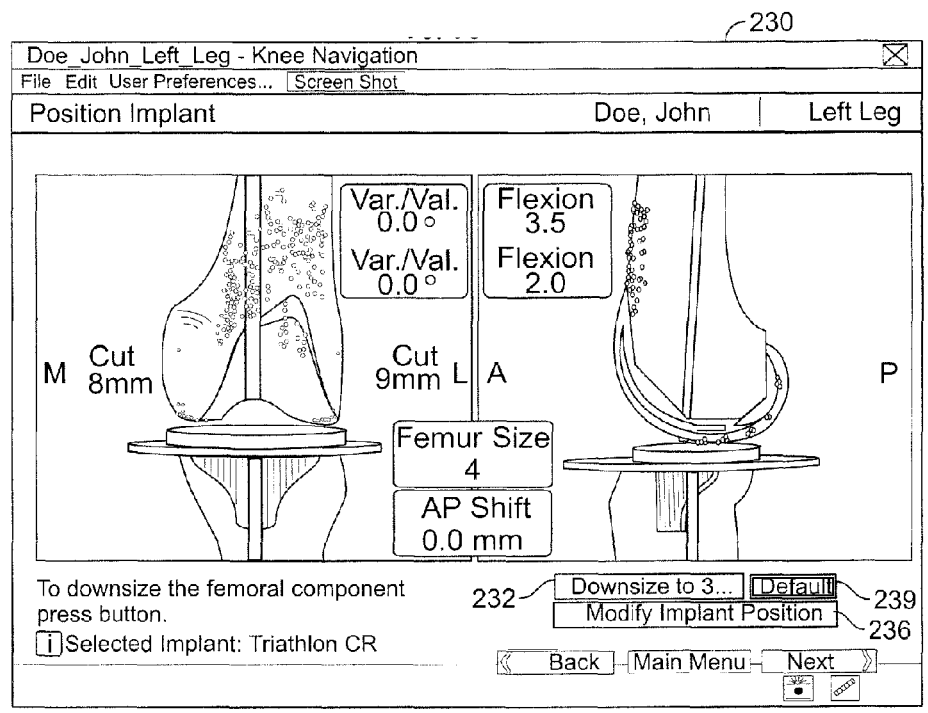
FIG. 11 is a screen shot showing another aspect of the implant position and sizing feature of the system.
Figure 12:
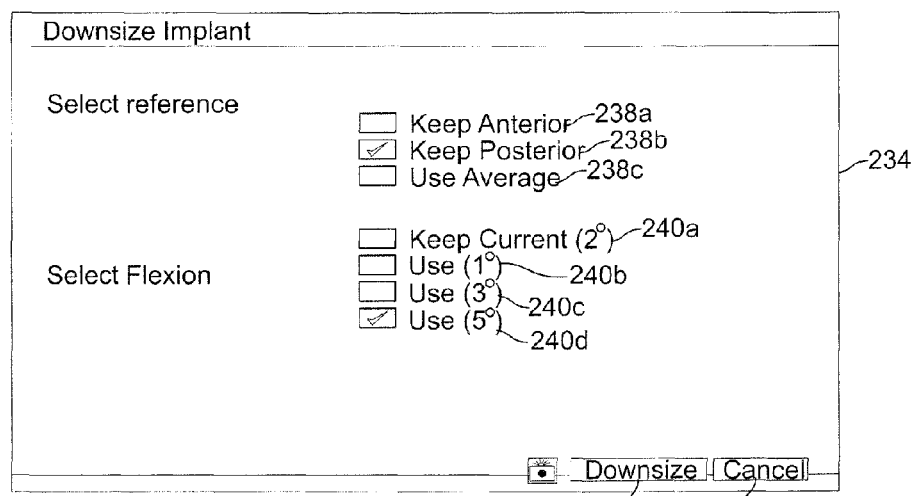
FIG. 12 is a screen shot showing a manual modification feature of the system.
Figure 13:
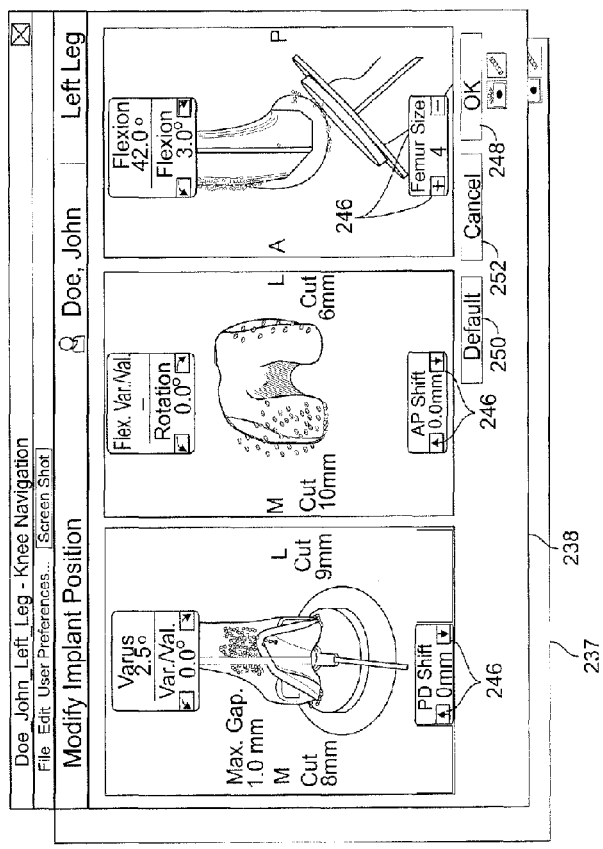
FIG. 13 is a screen shot showing another manual modification feature of the system.

The position implant routine 86 is initiated by selecting the appropriate button 206 from the main menu 202, which will automatically calculate the automatically calculated optimal implant size and position plan and display the results in a graphic representation of the bones and implants and in a numerical form in a position implant screen 230 as shown in FIG. 11, showing the selected implant positioned on the bone in the manner obtained from the calculations. This allows the surgeon to verify, both visually and from the various shown numerical data, whether the automatically calculated size, position, and alignment of the femoral implant is acceptable. The display also shows visual indicators on the graphic representation of the bones and implants to show areas of a designed anterior cortex resection that are left uncovered by the femoral implant, any gaps between the implant and uncut areas of the anterior cortex, and a position of a maximum gap between the femoral implant and uncut areas of the anterior cortex identical to the same indicators shown on the position implant screen. The position implant screen 230 shows the actual varus/valgus and flexion alignments of the leg, as determined from the registration routines, and the calculated design parameters for the femoral implant, including size, flexion, A/P shift, varus/valgus angle, rotation angle, distal resection level, and posterior resection level. The position implant screen also shows the implant system and type that was previously selected for the automatic size and position calculations and are shown in the design. The position implant screen 230 includes a downsize button 232 that, when selected, initiates the downsize implant subroutine 102 and changes the display to a downsize implant screen 234 as shown in FIG. 12. The position implant screen further includes a modify implant position button 236 that, when selected, initiates the modify implant position subroutine 104 and changes the display to a modify implant position screen 237 as shown in FIG. 13. A default button 239 may be selected at any time to return the size and position plan displayed on the screen to the automatically optimized size and position plan.

Turning now to FIG. 12, the downsize implant screen 234 displays choices for the surgeon to select to perform the first manual mode adjustments described previously herein. Specifically, three alternative selection boxes, 238a, 238b, and 238c, are displayed that allow the surgeon to choose between maintaining the anterior position, the posterior position or the average position of the design shown on the position implant screen during the downsize implant subroutine 102. Another four alternative selection boxes, 240a, 240b, 240c, and 240d, are displayed that allow the surgeon to choose between maintaining the flexion angle currently shown on the position implant screen or to choose one of three alternative flexion angles during the downsize implant subroutine 102. The selection box 240a associated with maintaining the flexion angle displays the current angle design. When the desired selections are indicated, a downsize button 242 is selected by the surgeon, and the computer automatically updates the size and position calculations based on the selected reference AR shift, reference flexion angle, and form-factor data for the incrementally lower implant size from the current design implant parameters to provide the modified implant size and position plan. The display on the position implant screen 230 is automatically updated to correspond with the modified implant size and position plan when the downsize button 242 is selected and shows a visual indicator if the fit assessment is calculated to produce a notch as described previously herein. A cancel button 244 is also displayed, which allows the surgeon to return to the position implant screen 230 without saving any changes to the previously displayed implant size and position plan.

Turning now to FIG. 13, the modify implant screen 237 graphically displays the femoral implant 18 and the tibial implant 20 superimposed on the appropriate bones in accordance with the current implant size and position plan parameters. The modify implant screen 237 also displays choices for the surgeon to select to perform the modify implant position subroutine 104 adjustments described previously herein. Specifically, the bones are shown in the actual position and alignments thereof and the implants are shown superimposed on the bones in the position of the current design. The display also shows the same visual indicators as in the position implant screen 230 to show areas of a designed anterior cortex resection that are left uncovered by the femoral implant, any gaps between the implant and uncut areas of the anterior cortex, and a position of a maximum gap between the femoral implant and uncut areas of the anterior cortex identical to the same indicators shown on the position implant screen. Increase/decrease arrow control button pairs 246 are displayed, which may be selected by the surgeon, for each of six degrees of freedom of the femoral implant, including varus/valgus angle, proximal/distal shift distance, rotation angle, anterior/posterior shift distance, flexion angle, and femoral implant size. Using the increase/decrease arrow control button pairs 246, the surgeon may manually alter each design parameter as desired, for example, to modify the automatically calculated optimal implant size and position plan and/or the modified implant size and position plan obtained from the downsize implant screen 234 to adapt such designs to allow for soft tissue considerations, which are not taken into consideration by the automatic mode for calculating the optimal implant size and position. In a similar manner as with the downsize implant screen, the position implant screen 230 is immediately updated to reflect a modified implant design position from the manually altered parameters selected on the modify implant position screen when an OK button 248 is selected. A default button 250 and a cancel button 252 are also displayed, which allow the surgeon to, respectively, return the design to the automatically calculated optimal implant design or return to the position implant screen without saving any changes made thereon.

After the surgeon has chosen a final design from the various designs described immediately herein-above, the remaining routines use the final design to guide the surgeon through the remaining steps for actually installing the prostheses on the patient in a manner known in the art.

Figure 14:
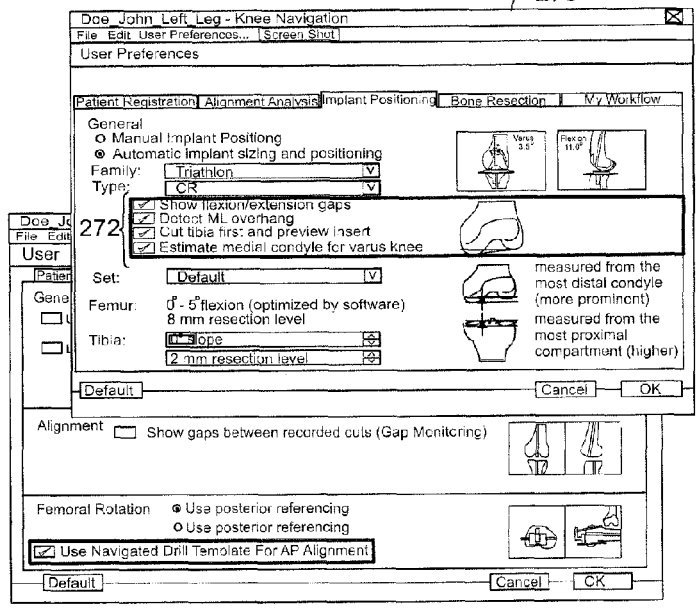
FIG. 14 shows screen shots of additional features of the system.

Turning to FIG. 14, a user preferences screen shot on a display screen 270 of a computerized system of the present disclosure is disclosed. When selecting Automatic implant sizing and positioning, the following features can be also selected optionally or in addition: show flexion/extension gaps feature, detect M/L overhang feature, cut tibia first and preview insert feature, estimate medial condyle for varus knee feature, use navigated drill template for A/P alignment feature, and/or show flexion/extension gap feature. Each feature may be selected using an appropriate button or dialog box 272.

Figure 15:
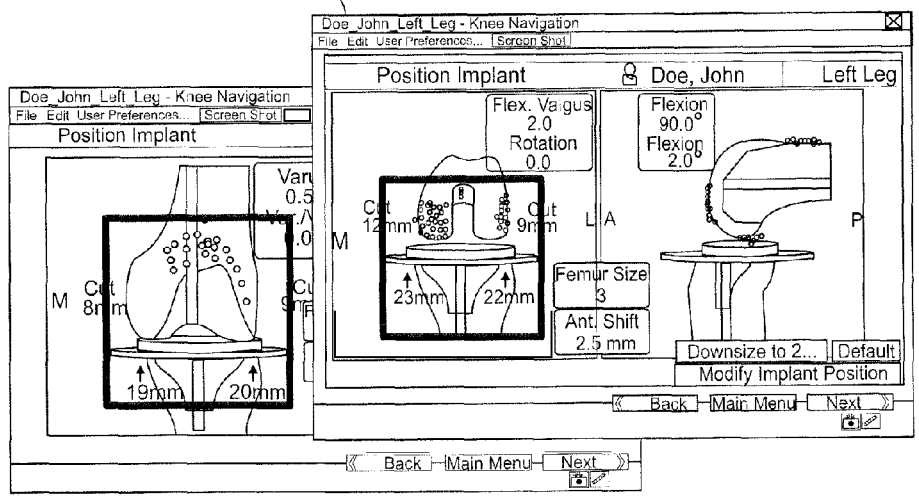
FIG. 15 shows screen shots of an implant positioning feature of the system.
Figure 21:
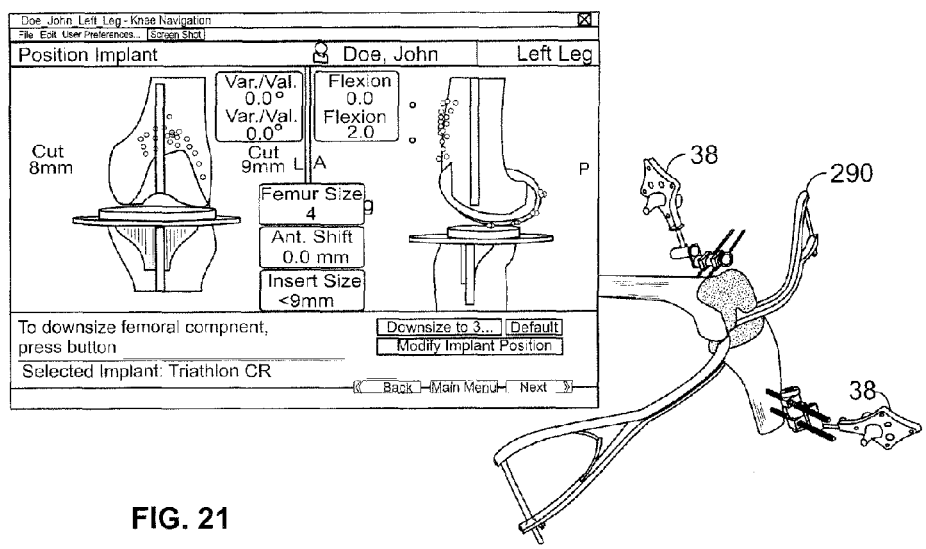
FIG. 21 shows a screen shot of the implant positioning feature and a diagrammatic view of a resected knee joint with a spreader inserted therein.

As shown in FIG. 15, the show flexion/extension gap button gives a preview on the size of the flexion and extension gap both for the medial and lateral side before any cuts are made. This allows the surgeon to assess whether the planned resections provide sufficient space for the intended implants. To get a proper preview of the gaps, it is advisable to ensure that the knee joint is distracted with any mechanical device such as a balancer or spreaders (FIG. 21). A proper preview of the flexion gap is given if the knee is distracted in flexion. The extension gap is shown if the knee is distracted in extension.

Figure 16A:
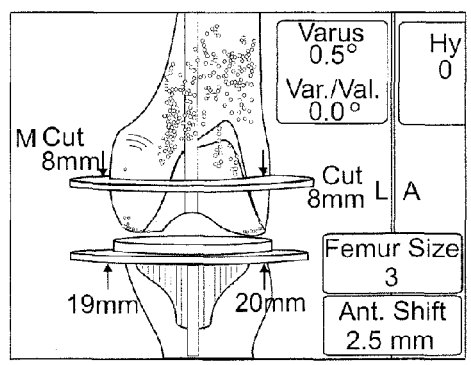
FIGS. 16A and 16B show detailed portions of a screen shot of FIG. 15.
Figure 16B:
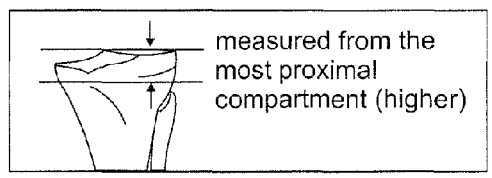

Turning now to FIGS. 16A and 16B, a detailed view of a screen shot associated with the show flexion/extension gaps feature shows the flexion/extension gap and the preview of the tibial resection. The preview of the gap size is based upon the calculated distal (and posterior) femur resection level and the tibial resection level. For the preview, in one embodiment, the tibial resection level by default is set to 8 mm measured from the most proximal (higher) compartment as long as the tibia is not resected and the cut not recorded.

Figure 17:
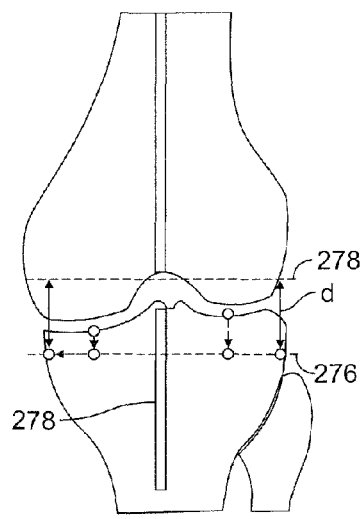
FIG. 17 is a diagrammatic view of a knee joint that shows flexion and extension gaps.

With reference to FIG. 17, the flexion/extension gaps are calculated in the following manner. First, the centers of mass of the digitized compartments are calculated. These centers of mass are then projected onto a tibial resection plane 276. The projected centers of mass are next translated medial/lateral by the factor 1.53. A line perpendicular to the tibial cutting plane passing through the projected and translated center of mass and intersecting with a femoral cutting plane 278 is drawn, and a distance "d" between the femoral and tibial cutting planes along this line is measured.

Turning now to FIG. 18, the detect ML overhang feature, according to one embodiment, includes a step of obtaining the AP position of the relevant medial and lateral overhang region where implant overhang may occur, such as by digitization of the subject surfaces. When digitizing, for example, the surgeon may start at the relevant AP position of the medial/lateral cartilage boundary and move the pointer tip proximally to describe a line. In the "Position Implant" dialog the average width of medial/lateral implant overhang or width of uncovered bone is displayed as a numerical value. In one aspect of the disclosure, potential medial/lateral overhang or uncovered bone is not considered in the automatic sizing and positioning calculations. In one embodiment, with reference to FIG. 19, when in the detect ML overhang feature, a portion of ML implant overhang/uncovered bone 280 is measured at the AP position of the digitized overhang region, the AP position of the relevant overhang region is determined by the surgeon, and only the average width of the medial/lateral overhang or uncovered bone is numerically displayed. Calculations of the ML overhang are then based upon a planned femoral implant 282. In another embodiment (not shown) the potential medial/lateral implant overhang or uncovered bone is considered in the automatic sizing and forms another fit criterion.

Figure 20:
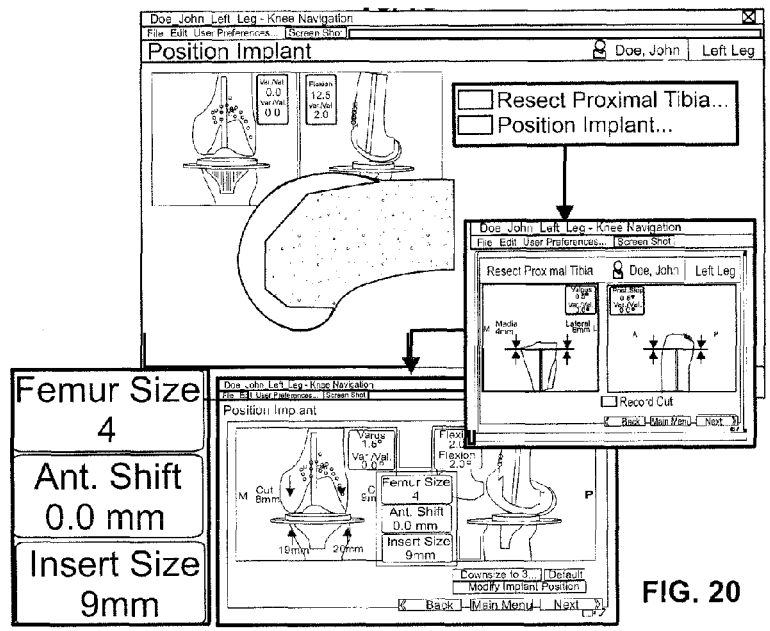
FIG. 20 shows screen shots of a reset proximal tibia feature of the system.

FIG. 20 shows screen shots for the cut tibia first and preview insert feature. If the cut tibia first and preview insert feature is selected, the software workflow (dialog box 286) prompts the user to cut the proximal tibia first before a Position Implant dialog box 288 is displayed. With the proximal tibia cut made and recorded, the Position Implant dialog box 288 gives a preview of what insert size (thickness) fits between the actual proximal tibia cut and the planned femoral implant.

Figure 22:
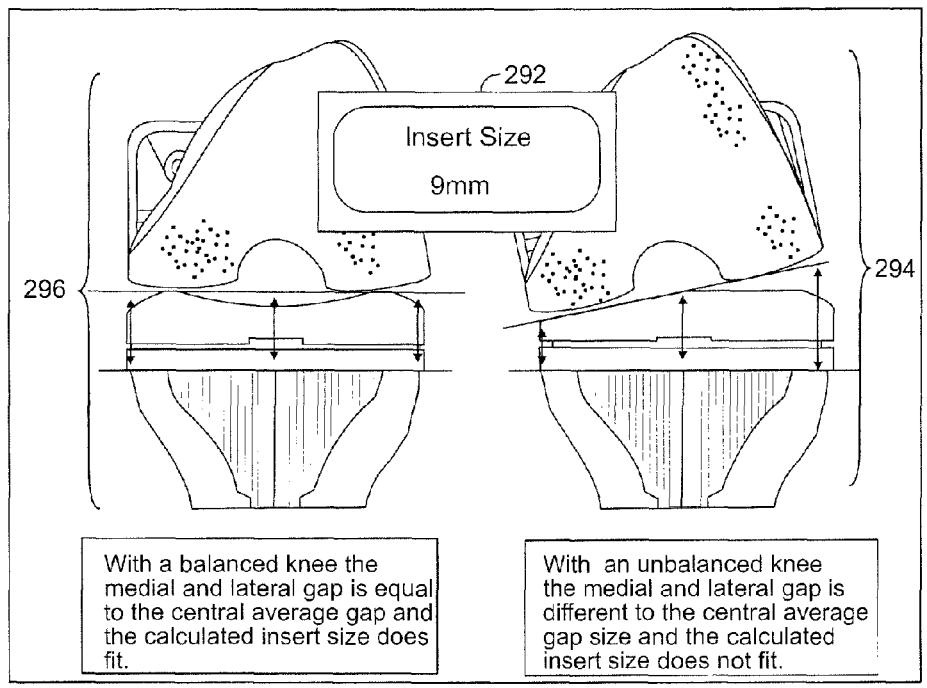
FIG. 22 is a diagrammatic representation of another aspect of the system.

With reference to the FIG. 21, during the cut tibia first and preview insert feature, to get a proper preview of the insert size, the knee joint is preferably distracted with any kind of balancer or spreader 290. The preview of the tibial implant size is given for the knee both in extension and in flexion. The preview and calculation of the tibial implant is based upon the recorded proximal tibia cut and the calculated/planned distal and posterior resection levels. The software causes a visual indicator to be shown on the display screen if the smallest available implant does not fit between the proximal tibia cut and the planned femoral implant, both for flexion and extension. Further, with reference to FIG. 22, the calculated tibial implant size shown in a box 292 reflects the average medial/lateral gap size only. For an unbalanced knee 294 with varus/valgus misalignment larger than 3° the calculated implant size would not fit into the tighter gap. For the calculated implant to fit into the gap, the ligaments preferably are balanced. With a balanced knee 296, the medial and lateral gap is equal to the central average gap and the calculated implant size fits. With the unbalanced knee 294, the medial and lateral gap sizes are different than the central average gap size and the calculated insert size does not fit.

Figure 23:
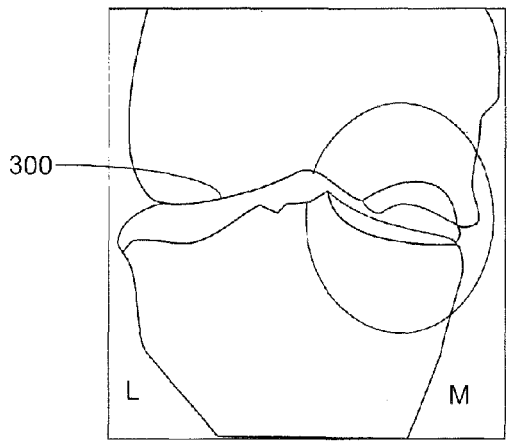
FIG. 23 is a diagrammatic representation of an x-ray photograph of a damaged knee joint.
Figure 24:
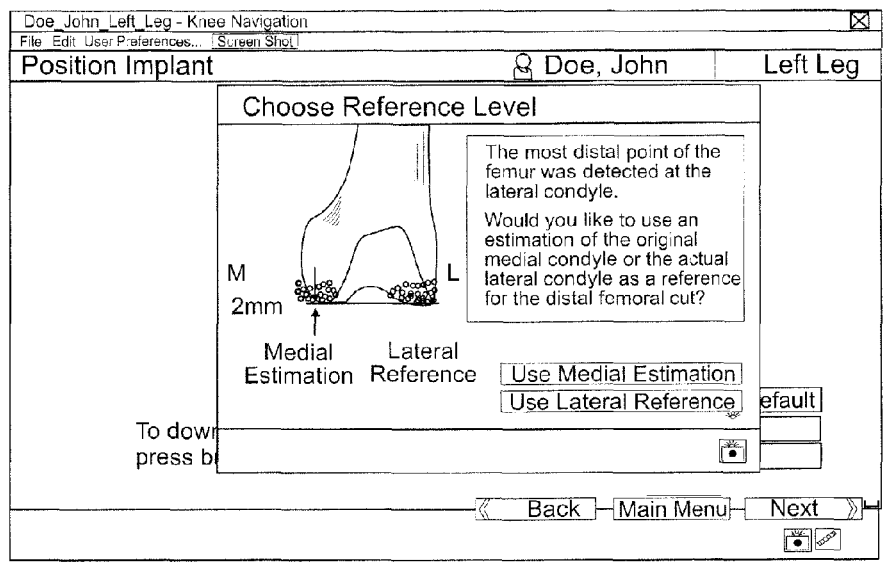
FIG. 24 shows a screen shot of still another aspect of the system.
Figure 25:
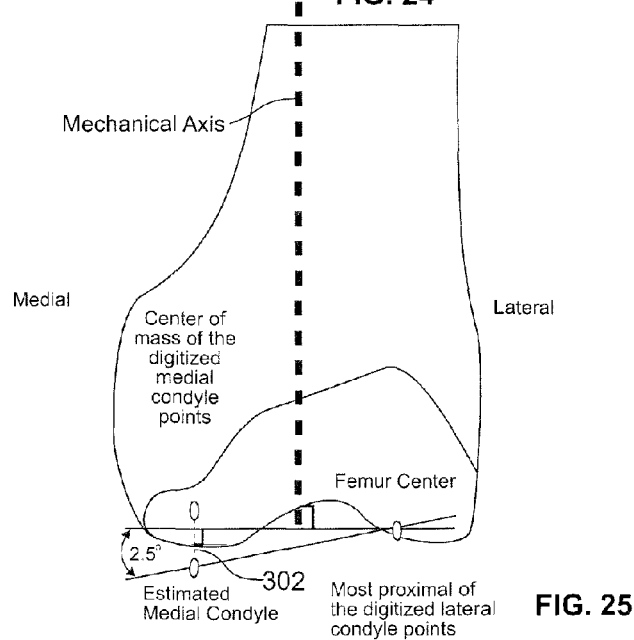
FIG. 25 is a diagrammatic representation of a distal end of a femur including biomechanical information superimposed thereover.
Figure 26:
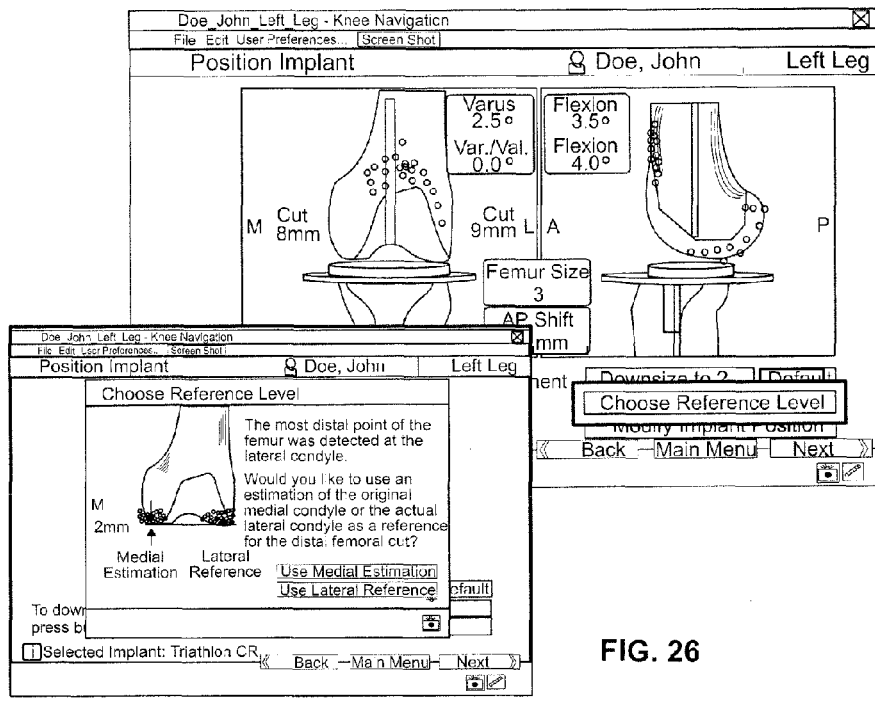
FIG. 26 shows a screen shot of yet a further aspect of the system.

Referring now to FIG. 23, one aim of a total knee arthroscopy is to reconstruct the original joint line 300. Using the estimate medial condyle for varus knee feature, joint line reconstruction (respectively resection level determination) is generally done with respect to the more prominent medial condyle. In case of varus deformities, however, the medial condyle can be severely damaged, and referencing of a severely damaged medial condyle could result in over-resecting the femur and a proximal shift of the original joint line. With the estimate medial condyle for varus knee feature activated, the software alerts the user if the medial condyle is severely damaged as shown with a visual alert on the display screen in FIG. 24. Severe damage is assumed to exist by the software if the digitized lateral condyle is more prominent than the digitized medial one. With the alert, the software offers the user an opportunity to either estimate the original medial condyle as reference for the distal femur resection level or to continue with the more prominent lateral side as reference for calculating the implant. In the estimate medial condyle for varus knee feature, with reference to FIG. 25, the applied angle 302 to estimate the medial condyle is set at 2.5° in one embodiment of the disclosure. Further, with reference to FIG. 26, the reference level can also be changed within the Position Implant dialog using the "Choose Reference Level" button after the optimal implant size and position plan is calculated by the software. When changing the reference level, the software repeats the calculation of the implant size, flexion and A/P position. In one embodiment of the disclosure, any modification (e.g. downsizing, changing A/P shift etc.) that may have been performed before will be lost and are overwritten by the new default position.

Figure 27:
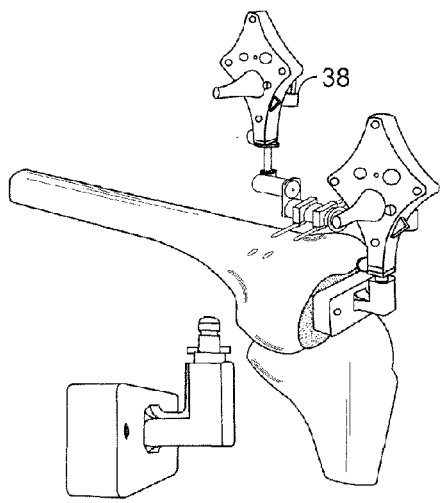
FIG. 27 is a diagrammatic representation of a knee joint with surgical tools for use during a total knee replacement surgical procedure.
Figure 28:
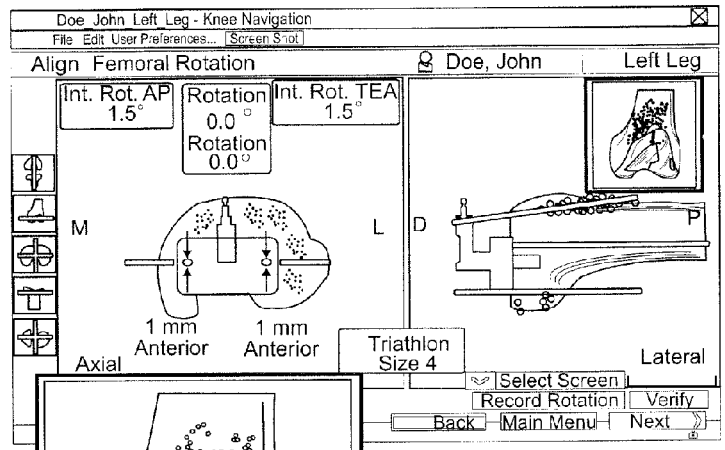
FIG. 28 shows screen shots of a further aspect of the system.

As shown in FIG. 27, navigated drill templates for A/P alignment (such as those available from Stryker Navigation of Freiburg, Germany) can be used to navigate and prepare for the rotational alignment and A/P position of a 4-in-1 cutting block. The navigated drill templates can replace a conventional A/P sizer. In contrast to a conventional A/P sizer, the navigated drill templates may be both simple to use and offer higher flexibility regarding A/P shifts without requiring adjustments at the instrument. In one embodiment of the disclosure, navigated drill templates can be selected in a user settings portion of the system if automatic sizing is enabled. With navigated drill templates, as shown most clearly in FIG. 28, the software facilitates to navigate two degrees of freedoms: rotational alignment and A/P position. In one embodiment, the rotational alignment is calculated with respect to the averaged rotation axis, the femoral A/P axis, and the transepicondylar line, and the reference for the AP position is the calculated implant and the virtual peg holes, which are displayed on the display screen. The deviation of the template of the virtual peg holes is also displayed on the display screen. In addition, a frontal view of the anterior cortex is displayed giving a preview of the position and size of the uncovered bone resection against the given flexion/extension of the distal femur cut and the A/P implant position. In one embodiment, the medial lateral position cannot be navigated.

Figure 29:
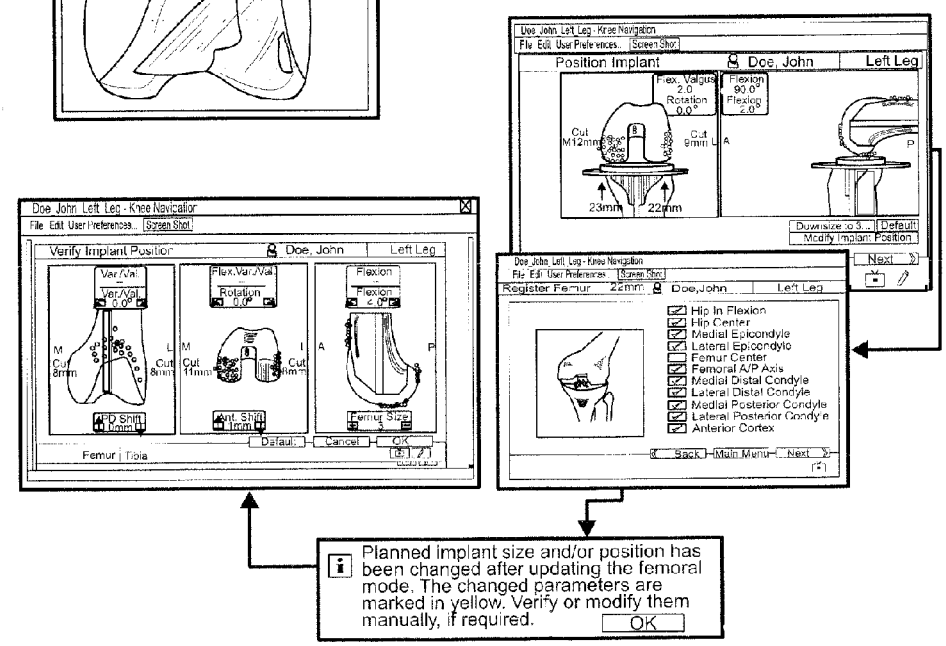
FIG. 29 shows screen shots of yet a further aspect of the system.

Turning now to FIG. 29, in one embodiment, if any femoral landmarks are redigitized after the optimal implant size and position plan is calculated, the software repeats the implant calculation and prompts the user to verify the changed implant parameter. To do so, the verify implant position dialog, shown in FIG. 16, is opened with the changed parameter displayed in yellow.

Although the foregoing detailed description is directed to a total knee replacement surgery using a navigation system, the method and system disclosed herein may be readily adapted for use at least in other surgical procedures where a prosthetic device must be selected from a plurality of different sizes and/or shapes and then positioned to meet user identified constraints. The method and system may also be readily adapted for use in other surgical procedures, and it is understood that the scope of the present disclosure is not limited to the specific surgical procedures described in detail herein. Further, the particular method of gathering anatomy data, such as the survey data of the bone to be resected, is not limited to direct digitization during the procedure. Rather, the anatomy data may be obtained any pre-operative method capable of acquiring the necessary anatomical shape data, such as X-ray scan, MRI scan, CT scan, ultra-sonic scan, and other pre-operative methods, other intra-operative methods, such as indirect digitization, a navigated probe and stylus, using optical, mechanical, or similar localizers, using range finders such as laser or moiré, and/or other data gathering techniques. In addition, execution of the final implant size and position plan to attach the implant is not limited to use of the navigational techniques disclosed herein. Rather, the implant may be attached according to the final implant size and position plan according to any method capable of satisfactorily executing the final plan.

Industrial Applicability

The technology of the present disclosure, in one embodiment, allows a surgeon to use a computer to quickly calculate an optimal prosthesis design based on patient information acquired during the surgical procedure that is calculated to optimize multiple design parameters, such as avoidance of notching and achieving enhanced match between an anterior implant contour and anterior cortex of a femur in a total knee replacement arthroplasty surgical procedure. The technology of the present disclosure also may be used to allow the surgeon to manually modify the automatically calculated optimal implant design to make adjustments as considered necessary to, for example, take into account soft tissue concerns based on the knowledge and experience of the surgeon. The technology of the present disclosure may, in some cases, help to avoid common problems, such as unnecessarily over sizing an implant, leaving an unnecessarily large amount of uncovered anterior bone resection, or having an unnecessarily large anterior overhang and gap between the anterior surface of the implant and uncut areas of the anterior cortex, which may be associated with prior methods such as simply choosing an implant design based on visual observations by the surgeon.

Numerous modifications to the present disclosure will be apparent to those skilled in the art in view of the foregoing description. Accordingly, this description is to be construed as illustrative only and is presented for the purpose of enabling those skilled in the art to make and use the disclosure and to teach the best mode of carrying out same. The exclusive rights to all modifications which come within the scope of the appended claims are reserved.

We claim:

1. A system for assessing a fit of a femoral implant to a distal end of a femur in a selected orientation prior to resecting the femur, wherein the system comprises:
   means for obtaining pre-defined form factor information for plurality of femoral implants;
   means for obtaining surface shape information of the distal end of the femur;
   means for automatically performing a virtual fit assessment of each possible incremental position of a pre-defined set of incremental positions for each size implant to be considered prior to resecting the femur; and
   means for selecting an optimal implant size and position from the virtual fit assessments.

2. The system of claim 1, wherein a target reconstruction position is defined based on design parameters for matching a selected varus or valgus angle, rotation angle, and surface position of posterior condyle and distal condyle of the femur.

3. The system of claim 1, wherein the means for selecting includes means for calculating maximum run out of an anterior resection of the femur from a proximal end contour of the femoral implant.

4. The system of claim 1, wherein the means for selecting includes means for calculating a percentage of the proximal end contour that lies on cut anterior cortex bone.

5. The system of claim 1, wherein the means for selecting includes means for calculating a percentage of the proximal end contour that lies on or above uncut anterior cortex bone.

6. The system of claim 1, wherein the means for selecting includes means for calculating a maximum gap between the femoral implant and the uncut anterior cortex bone.

7. The system of claim 1, wherein the means for selecting includes means for comparing each assessed fit with a weighted algorithm to identify an optimal implant size and position that minimizes notching of the bone and over sizing of the implant.

8. The system of claim 1, further comprising means for previewing a size of flexion and extension gap for a medial and lateral side.

9. The system of claim 1, further comprising means for detecting medial/lateral overhang.

10. The system of claim 1, further comprising means for cutting a proximal tibia and previewing an insert.

11. The system of claim 1, further comprising means for estimating medial condyle for varus knee.

12. The system of claim 1, further comprising means for using a navigated drill template for anterior/posterior alignment.

\* \* \* \* \*